(12) United States Patent
Casola et al.

(10) Patent No.: US 6,699,459 B2
(45) Date of Patent: Mar. 2, 2004

(54) METHODS OF TREATING LUNG INFLAMMATION

(75) Inventors: Antonella Casola, Galveston, TX (US); Roberto Garofalo, Galveston, TX (US); Allan R. Brasier, Galveston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 10/087,319

(22) Filed: Mar. 1, 2002

(65) Prior Publication Data

US 2003/0012736 A1 Jan. 16, 2003

Related U.S. Application Data

(60) Provisional application No. 60/272,501, filed on Mar. 1, 2001.

(51) Int. Cl.[7] ............... A61K 9/12; C09K 15/00
(52) U.S. Cl. ............... 424/45; 424/46; 514/826; 252/397
(58) Field of Search ............... 424/45, 46; 514/826; 252/397

(56) References Cited

U.S. PATENT DOCUMENTS

| | | |
|---|---|---|
| 5,340,803 A | 8/1994 | Rubin |
| 5,652,236 A | 7/1997 | Krauss |

OTHER PUBLICATIONS

Reimund et al "Antioxidants inhibit the in vitro production of inflammatory cytokines in Crohn's disease and ulcerative colitis", European Journal of Clinical Investigation (1998) 28, 145–150.*
Genin et al "Regulation of RANTES chemokine gene expression requires cooperativity between NF–Kappa B and IFN–regulatory factor transcription factors", J Immunol May 15, 2000; 164(10): 5352–61–13 Abstract.*
Mastronarde et al., Am. J. Respir. Cell Mol. Biol., 13:237–44(1995).
Mastronarde et al., J. Infect. Dis., 177(5):1275–81(1998)(abstract).
Schweizer et al., J. Gen. Virol., 80:1147–55(1999)(abstract).
Ribavirin , Factsheet, Federaltion of Nurses and Health Professionals (2001).

* cited by examiner

*Primary Examiner*—Michael G. Hartley
*Assistant Examiner*—M. Haghighatian
(74) *Attorney, Agent, or Firm*—Rogalsky & Weyand, LLP

(57) ABSTRACT

The present invention relates to a method of treating lung inflammation in a subject which includes administering butylated hydroxyanisol to the subject in an amount effective to treat lung inflammation. The invention also relates to methods of inhibiting interferon regulatory factor activation in a subject and in an alveolar cell. Another aspect of the invention relates to an assay.

33 Claims, 25 Drawing Sheets

Figure 1:
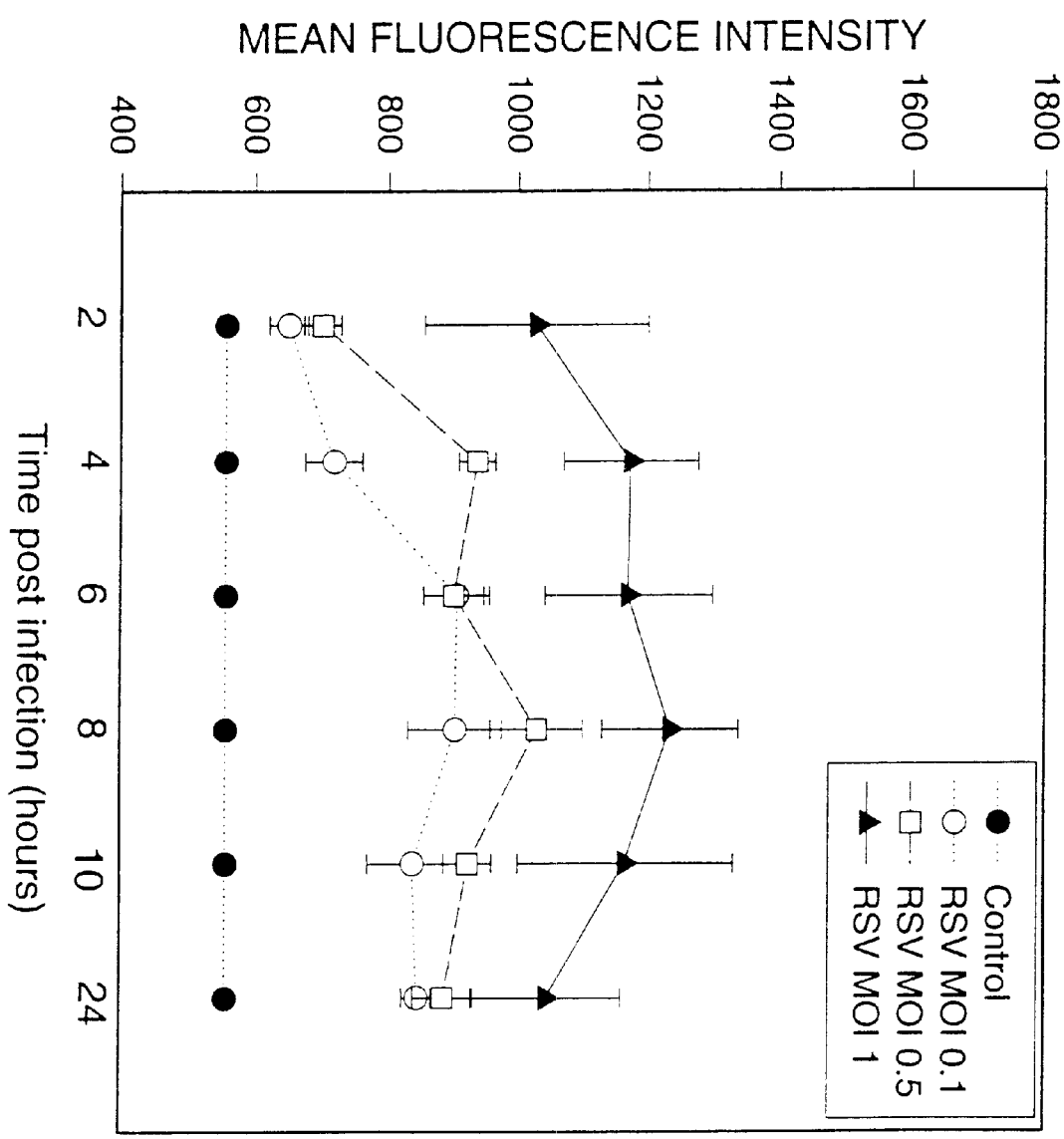

| RSV: | − | + | + |
|---|---|---|---|
| BHA: | − | − | + |

IRF-3

FIG. 10

BHA:
RSV:

IRF-1

IRF-3

IRF-7

METHODS OF TREATING LUNG INFLAMMATION

The present application claims priority of U.S. Provisional Patent Application Serial No. 60/272,501, filed Mar. 1, 2001, which is hereby incorporated by reference.

The present invention was made with the support of the National Institute of Health Contract Nos. P30ES06676, AI40218, AI15939, AI01763 and PO146004. The Federal Government may have certain rights in this invention.

BACKGROUND OF THE INVENTION

Throughout this application various publications are referenced, many in parentheses, with full citations in the references section. The disclosures of each of these publications in their entireties are hereby incorporated by reference in this application.

Respiratory syncytial virus (RSV) is an enveloped, negative-sense single-stranded RNA virus (1). Since its isolation, RSV has been identified as a leading cause of epidemic respiratory tract illness in children in the U.S. and worldwide. In fact, RSV is so ubiquitous that it will infect 100% of children before the age of 3. It is estimated that 40–50% of children hospitalized with bronchiolitis and 25% of children with pneumonia are infected with RSV, resulting in 100,000 hospital admissions annually in the US alone (1). In addition to acute morbidity, there are long-term consequences of RSV infection in infancy. RSV has been shown to predispose to the development of hyperreactive airway disease (2) and recurrent episodes of wheezing in asthmatic children are often precipitated by RSV infection. The mechanisms of RSV-induced airway disease and its long-term consequences are largely unknown, but the delicate balance between immunopathology and immunoprotection in the airway mucosa may be altered by an exuberant and unwanted local inflammatory response. Airway infiltration of monocytes and lymphocytes is typical of RSV infection (1), and activation of eosinophil and basophil leukocytes has been shown to correlate with the severity of acute RSV disease (3;4).

DETAILED DESCRIPTION OF THE DRAWINGS

FIG. 1. Time-course of ROS production in A549 cells infected with RSV. A549 cells were infected with RSV at three different multiplicity of infection (MOI). At various time points after infection, cells were loaded with DCF-DA and fluorescence was measured in control and infected cells. Mean Fluorescence Intensity is plotted as a function of time. The error bars represent SD from three independent experiments.

Figure 2A:
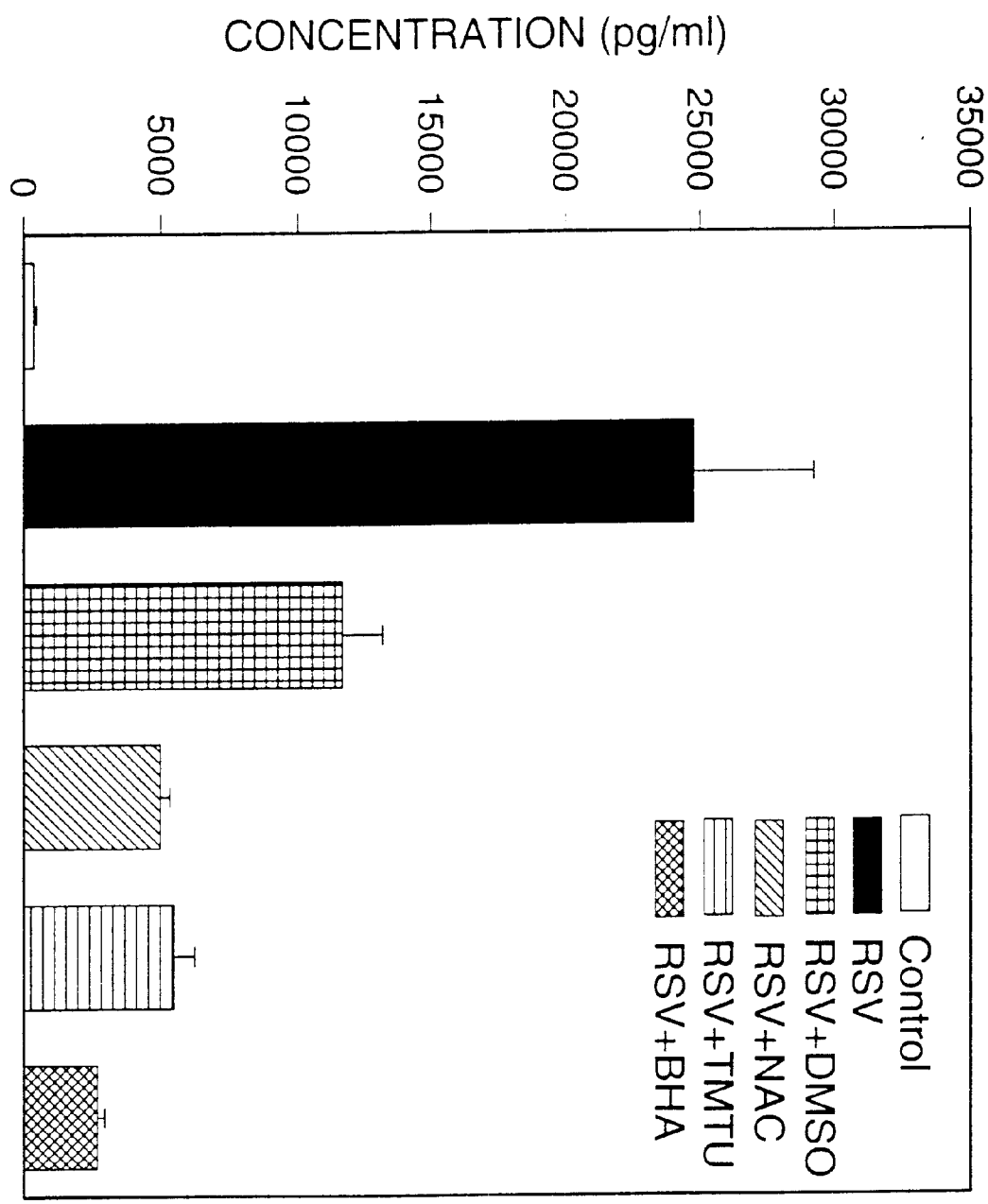
Figure 2B:
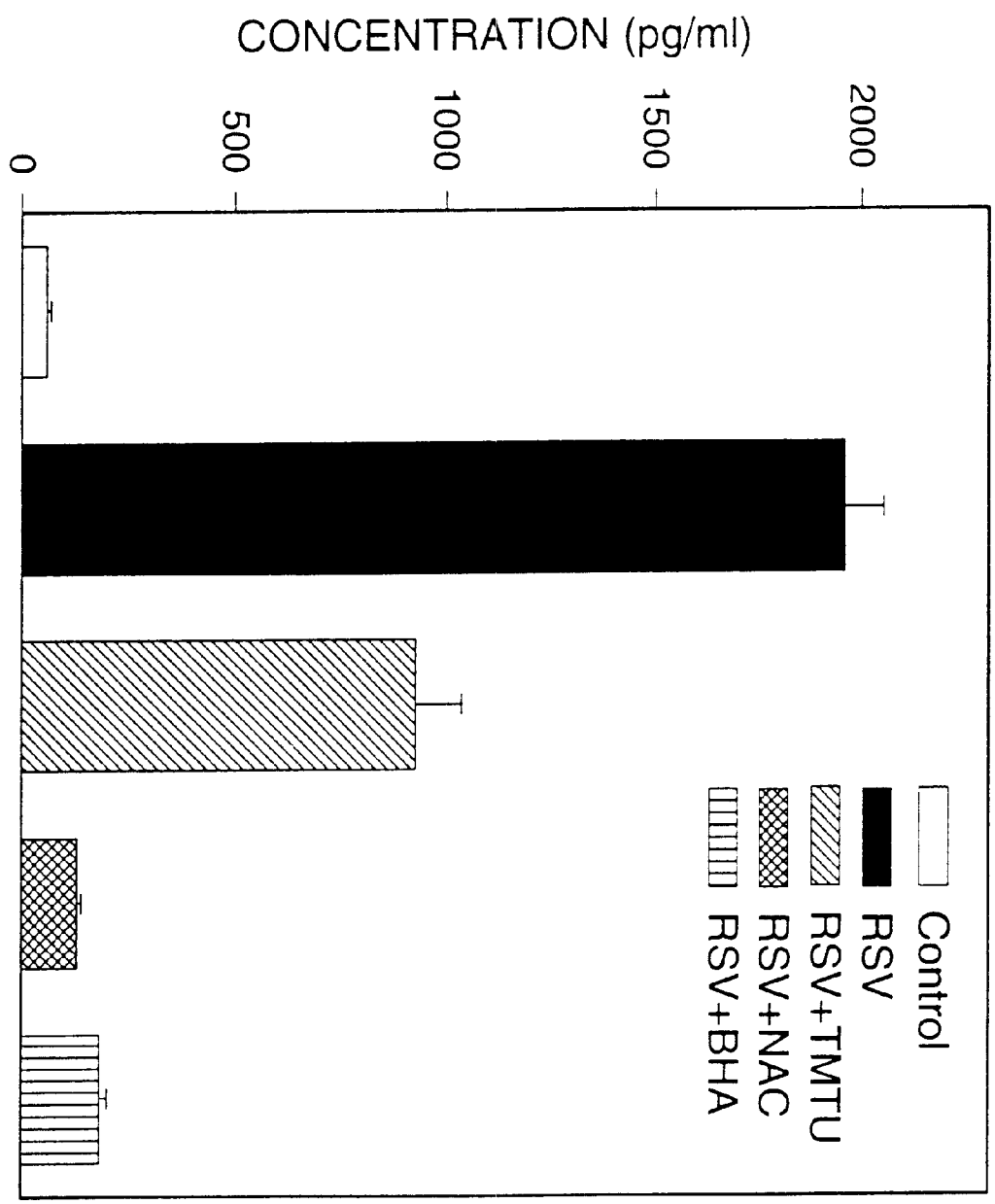

FIG. 2. Effect of antioxidants on RSV-induced RANTES (regulated upon activation, normal T-cells expressed and secreted) secretion. A549 cells (Panel A) or SAE cells (Panel B) were infected with RSV in the absence or presence of 2% (v/v) DMSO, 20 mM NAC, 20 mM TMTU and 400 $\mu$M BHA. Culture supernatants, from control and infected cells, were assayed 24 hours later for RANTES production by ELISA. Data are expressed as mean±standard deviation of three independent experiments performed in triplicates. *P<0.01 relative to RSV-infected cells not treated with BHA.

Figure 3:
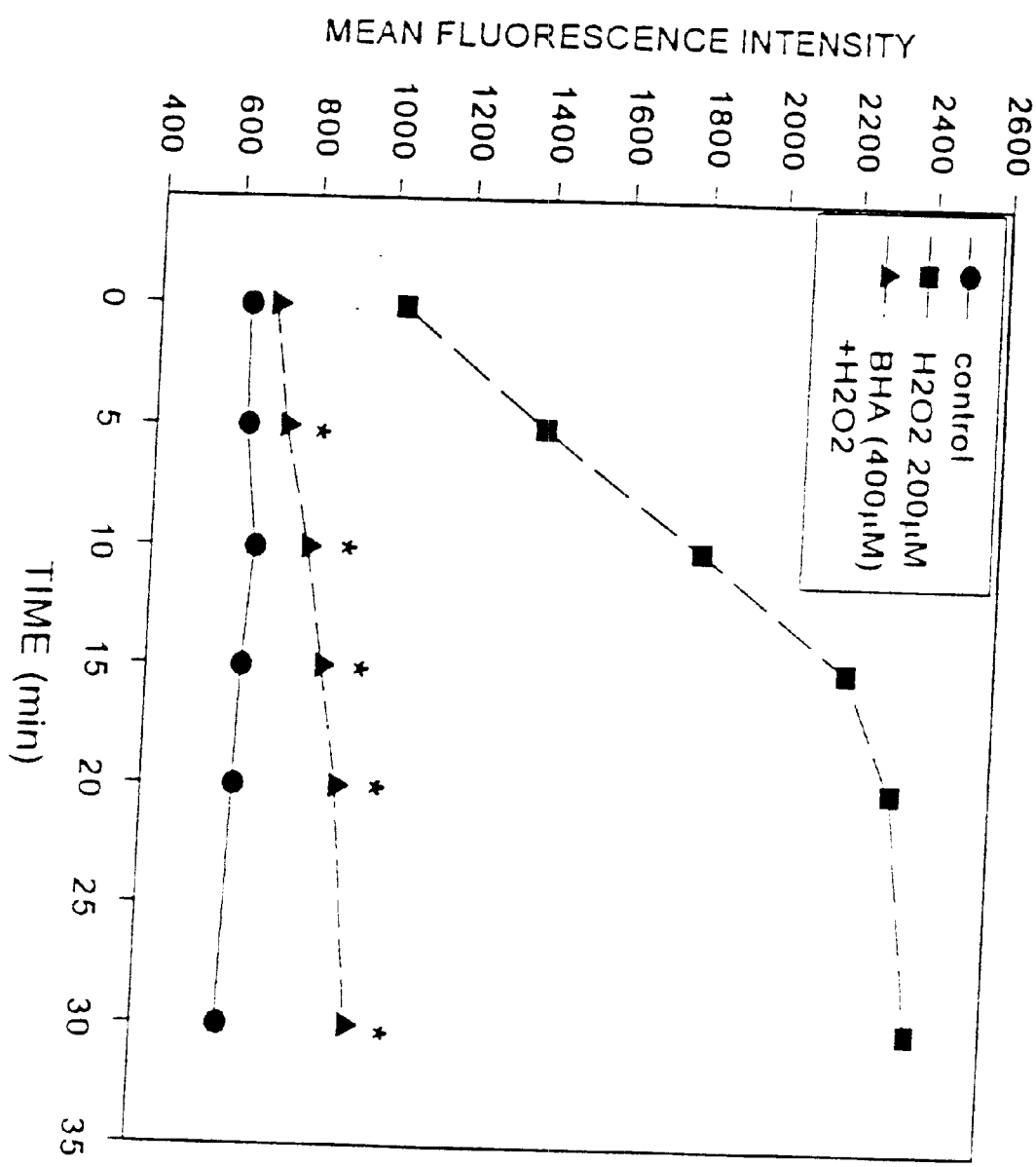

FIG. 3. BHA neutralization of $H_2O_2$-induced ROS production. DCF-DA loaded A549 cells were left untreated or stimulated with 200 $\mu$M $H_2O_2$ in the absence or presence of 400 $\mu$M BHA. Mean Fluorescence Intensity is plotted as a function of time. Data are representative of one of three independent experiments with similar results. *, P<0.01 relative to $H_2O_2$ only treated cells.

Figure 4:
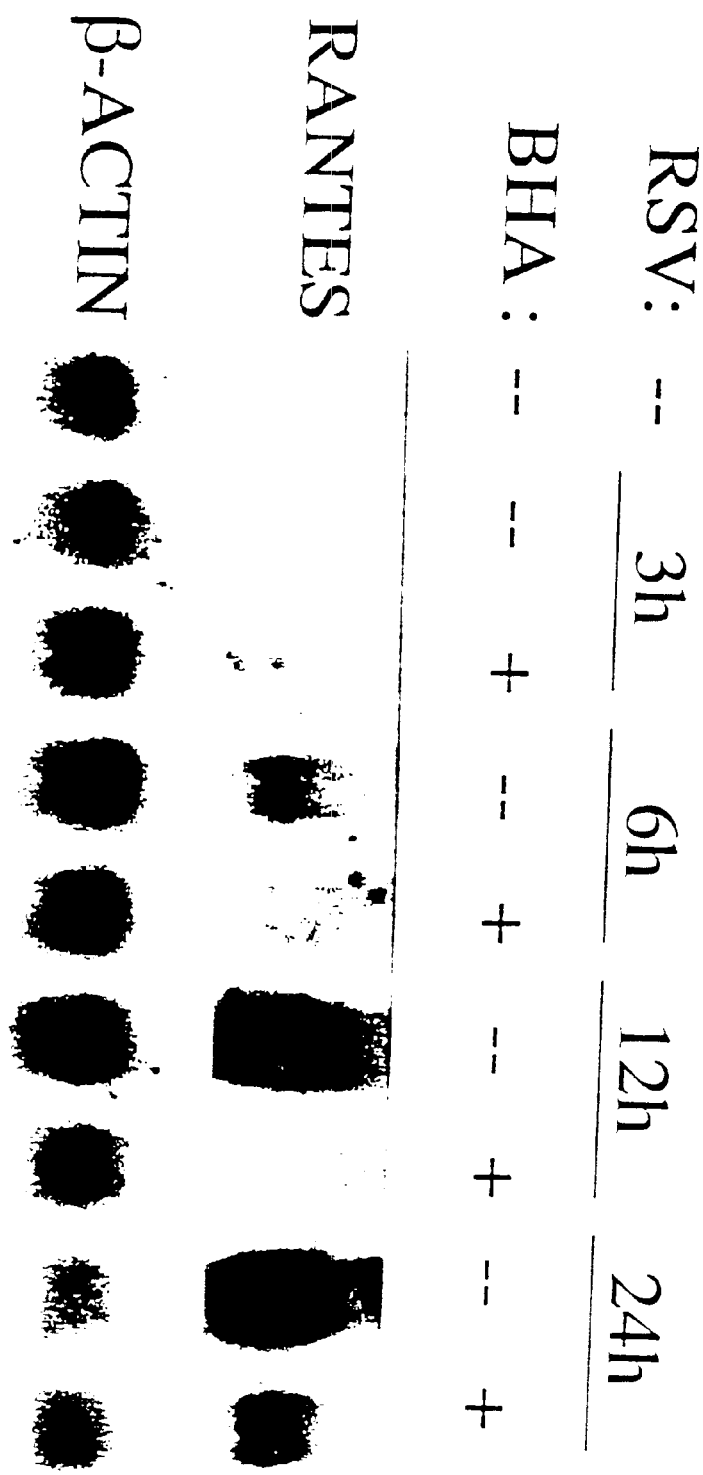

FIG. 4. Northern blot of RANTES mRNA in RSV-infected A549. A549 cells were infected with RSV for various lengths of time in the absence or presence of 400 $\mu$M BHA. Total RNA was extracted from control and infected cells and twenty micrograms of RNA were fractionated on a 1.2% agarose-formaldehyde gel, transferred to nylon membrane and hybridized to a radiolabeled RANTES cDNA probe. Membrane was stripped and hybridized with a radiolabeled $\beta$-actin probe, to show equal loading of the samples.

Figure 5:
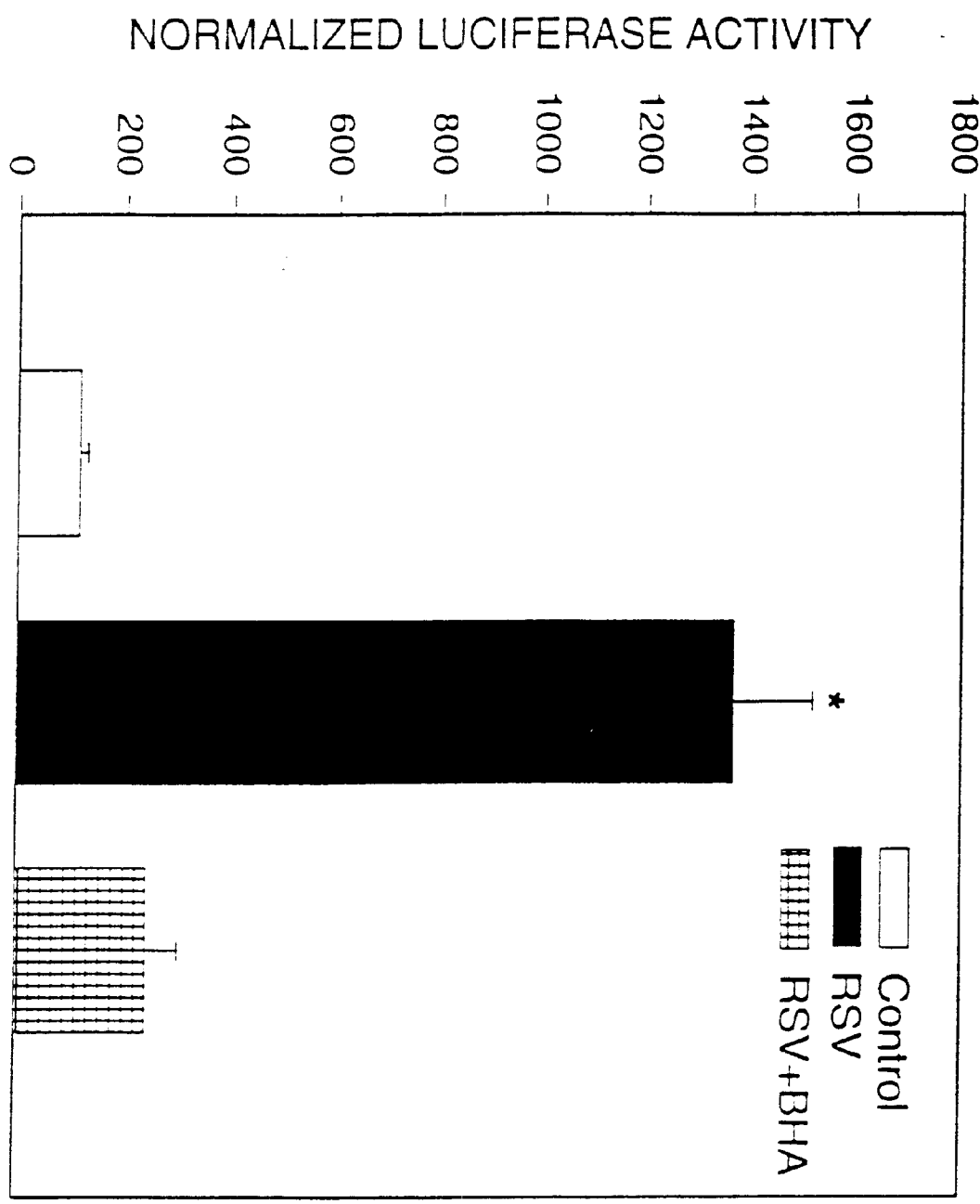

FIG. 5. Effect of BHA on RANTES promoter activation following RSV infection. A549 cells were transiently transfected with pGL2-220 plasmid and infected with RSV in the absence or presence of 400 $\mu$M BHA. At 24 hours post-infection, cells were harvested to measure luciferase activity. Uninfected plates served as controls. For each plate luciferase was normalized to the $\beta$-galactosidase reporter activity. Data are expressed as mean±standard deviation of normalized luciferase activity. *, P<0.01 relative to RSV-infected plates not treated with BHA.

Figure 6:
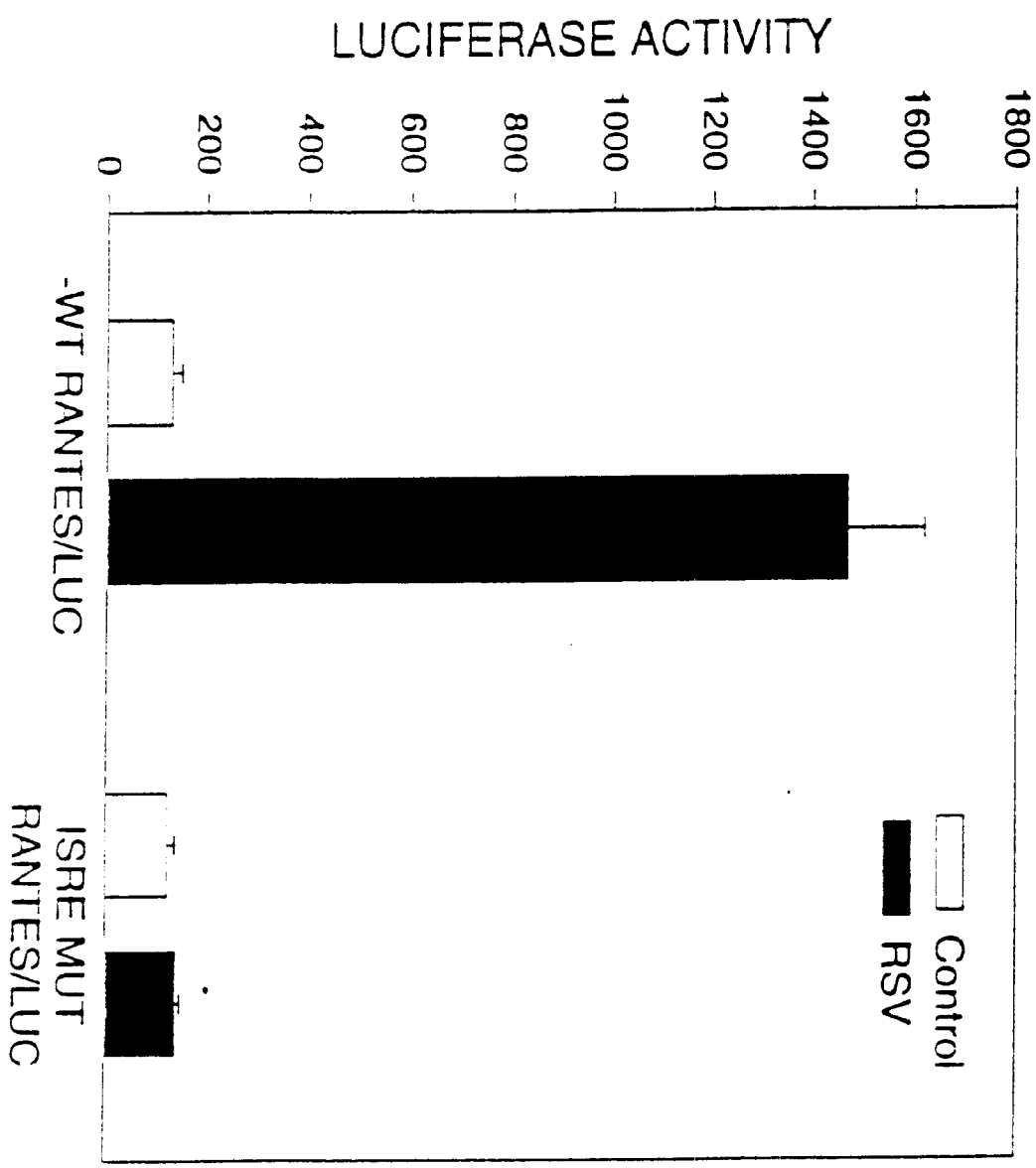

FIG. 6. Effect of site-mutations of RANTES promoter Interferon Stimulated Responsive Element (ISRE) on RSV-inducible luciferase activity. A549 cells were transiently transfected with pGL2-220 RANTES promoter either wild type (WT) or mutated (MUT) in the ISRE site and infected with RSV for 24 hours. Uninfected plates served as controls. For each plate luciferase was normalized to the $\beta$-galactosidase reporter activity. Data are expressed as mean±standard deviation of normalized luciferase activity.

Figure 7:
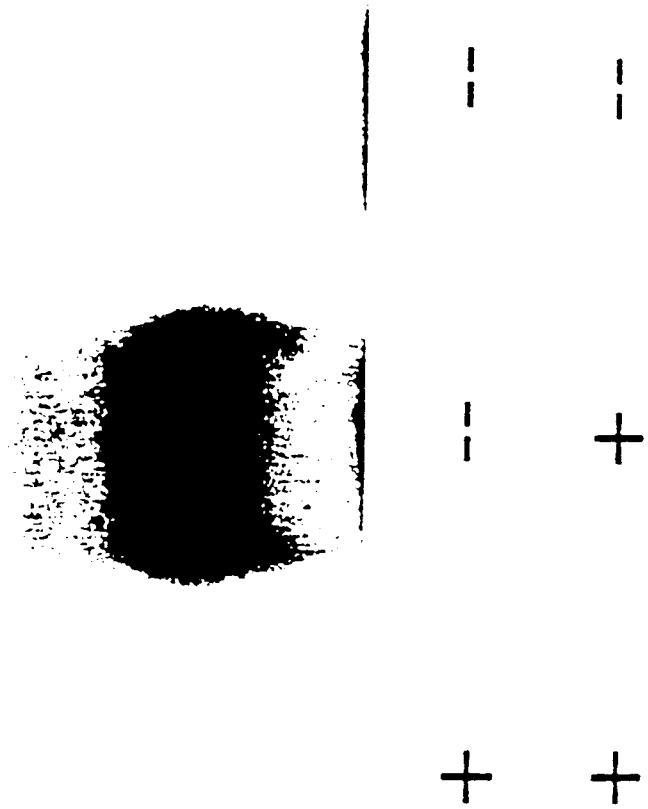

FIG. 7. Electrophoretic mobility shift assay (EMSA) of RANTES ISRE binding complexes in response to antioxidant treatment. Nuclear extracts were prepared from control and cells infected with RSV for 12 hours, in the absence or presence of 400 $\mu$M BHA, and used for binding to the RANTES ISRE in EMSA. Shown is the nucleoprotein complex formed on the RANTES ISRE in response to RSV infection.

Figure 8:
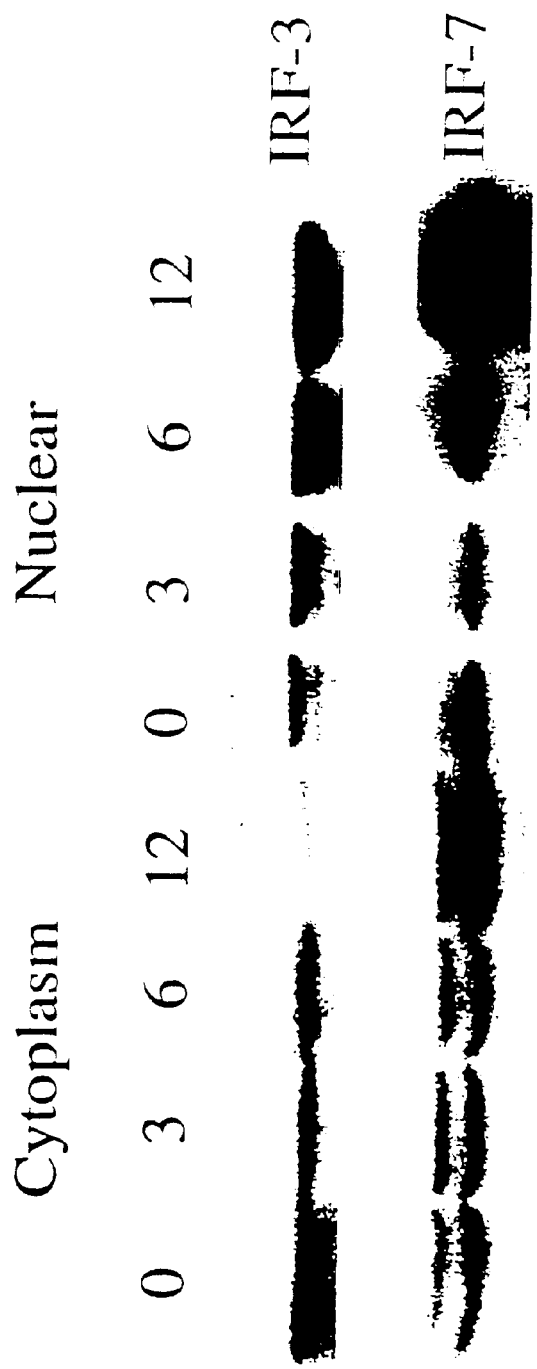

FIG. 8. Western blot of IRF-3 and -7 in RSV-infected A549 cells. Cytoplasmic and nuclear proteins were prepared from control and A549 cells infected for various length of time, fractionated on a 10% SDS-PAGE, transferred to PVDF membranes and probed with the appropriate antibody.

Figure 9:
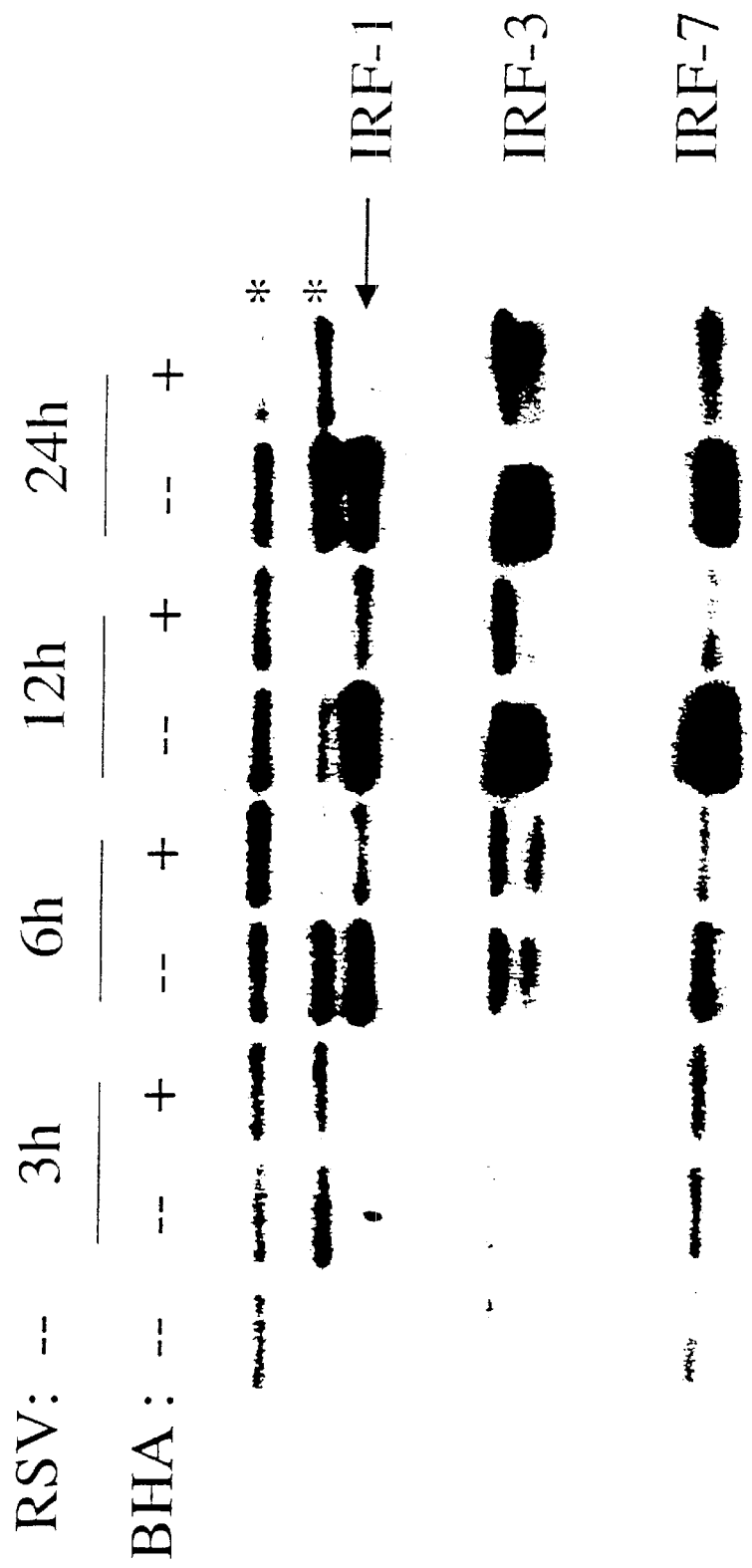

FIG. 9. Effect of BHA on IRF nuclear abundance in A549 cells infected with RSV. A549 cells were infected with RSV for 3, 6, 12 and 24 hours, in the absence or presence of 400 $\mu$M BHA. Cells were harvested to prepare nuclear extracts and equal amounts of protein from control and infected cells were assayed for IRF-1, -3 and -7 by Western blot. Arrows indicate the two nuclear forms of IRF-3 detectable after RSV infection.

Figure 10:
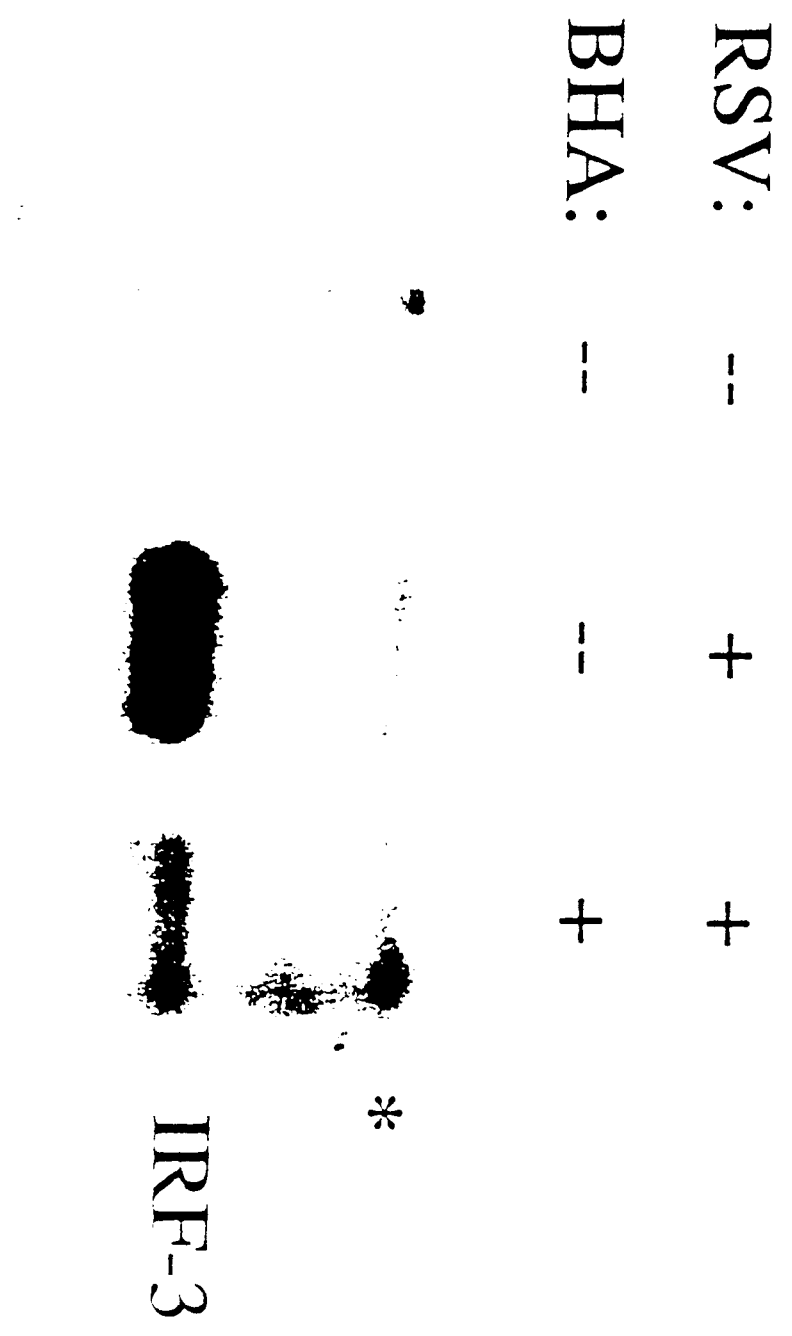

FIG. 10. Microaffinity isolation/Western blot for IRF-3. Nuclear extracts, prepared from A549 cells control and infected with RSV for 12 hours, in the absence or presence of BHA, were affinity purified using biotinylated ISRE oligonucleotide. After capture with streptavidin-agarose beads, complexes were eluted and assayed for IRF-3 by Western blot. * indicates a non-specific band.

Figure 11:
Figure 11:
Figure 11:

FIG. 11. Effect of BHA on IRF protein expression in A549 cells infected with RSV. A549 cells were infected with RSV for 12 hours, in the absence or presence of 400 $\mu$M BHA. Cells were harvested to prepare total cell lysates and equal amounts of protein from control and infected cells were assayed for IRF-1, -3 and -7 by Western blot. I, II, III and IV indicates the four different bands detected by the anti-IRF-3 antibody.

Figure 12:
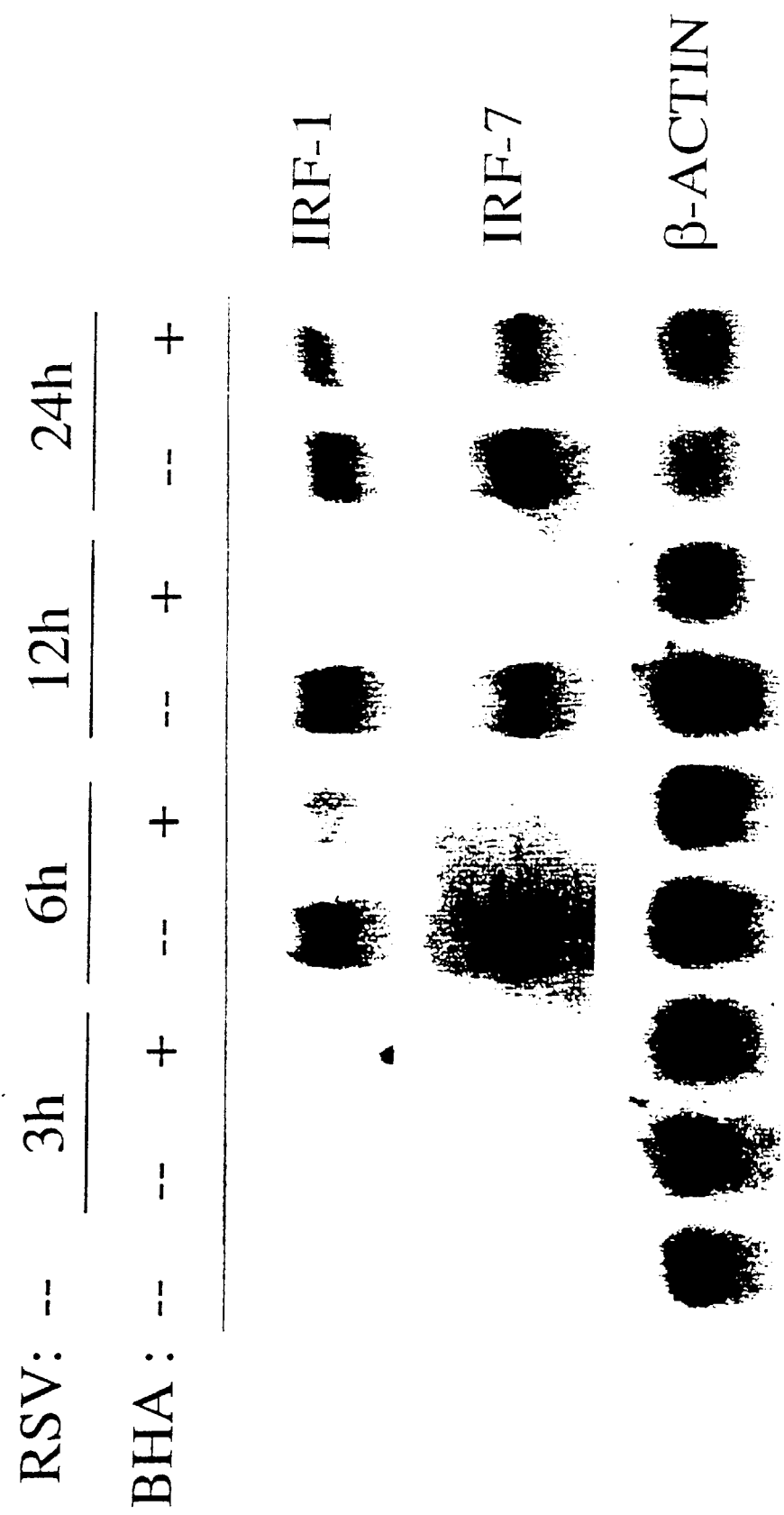

FIG. 12. Northern blot of IRF mRNA in RSV-infected A549. A549 cells were infected with RSV for various lengths of time in the absence or presence of 400 μM BHA. Total RNA was extracted from control and infected cells and twenty micrograms of RNA were fractionated on a 1.2% agarose-formaldehyde gel, transferred to nylon membrane and hybridized to a radiolabeled IRF-1 or -7 cDNA probe. Membrane was stripped and hybridized with a radiolabeled β-actin probe, to show equal loading of the samples.

FIG. 13. IRF-1 promoter activation following RSV infection. Panel A: time course. A549 cells were transiently transfected with the IRF-1 promoter plasmid and infected with RSV, MOI of 1. At different times post-infection, cells were harvested to measure luciferase activity. Uninfected plates served as controls. Panel B: effect of BHA. A549 cells were transfected with the IRF-1 promoter plasmid, infected with RSV for 12 hours, in the absence or presence of 400 μM BHA, and harvested to measure luciferase activity. For each plate luciferase was normalized to the β-galactosidase reporter activity. Data are expressed as mean±standard deviation of normalized luciferase activity.

FIG. 14. IRF-7 promoter activation following RSV infection. Panel A: time course. A549 cells were transiently transfected with the IRF-7 promoter plasmid and infected with RSV, MOI of 1. At different times post-infection, cells were harvested to measure luciferase activity. Uninfected plates served as controls. Panel B: effect of BHA. A549 cells were transfected with the IRF-7 promoter plasmid, infected with RSV for 6 hours, in the absence or presence of 400 μM BHA, and harvested to measure luciferase activity. For each plate luciferase was normalized to the β-galactosidase reporter activity. Data are expressed as mean±standard deviation of normalized luciferase activity.

FIG. 15. EMSA of IRF-1 GAS binding complexes in response to RSV infection. Panel A: autoradiogram of time course. Nuclear extracts were prepared from control and RSV-infected A549 cells at the indicated times and used for EMSA. Time (in hours) following RSV infection is indicated at top. Panel B: supershift-interference assay. Nuclear extracts of A549 cells infected for 6 hours were used in the EMSA in the presence of preimmune serum (PI), anti-STAT-1, -2, -3, -5 and anti-IRF-9 antibodies. Arrows indicates supershifted complexes.

Figure 16:
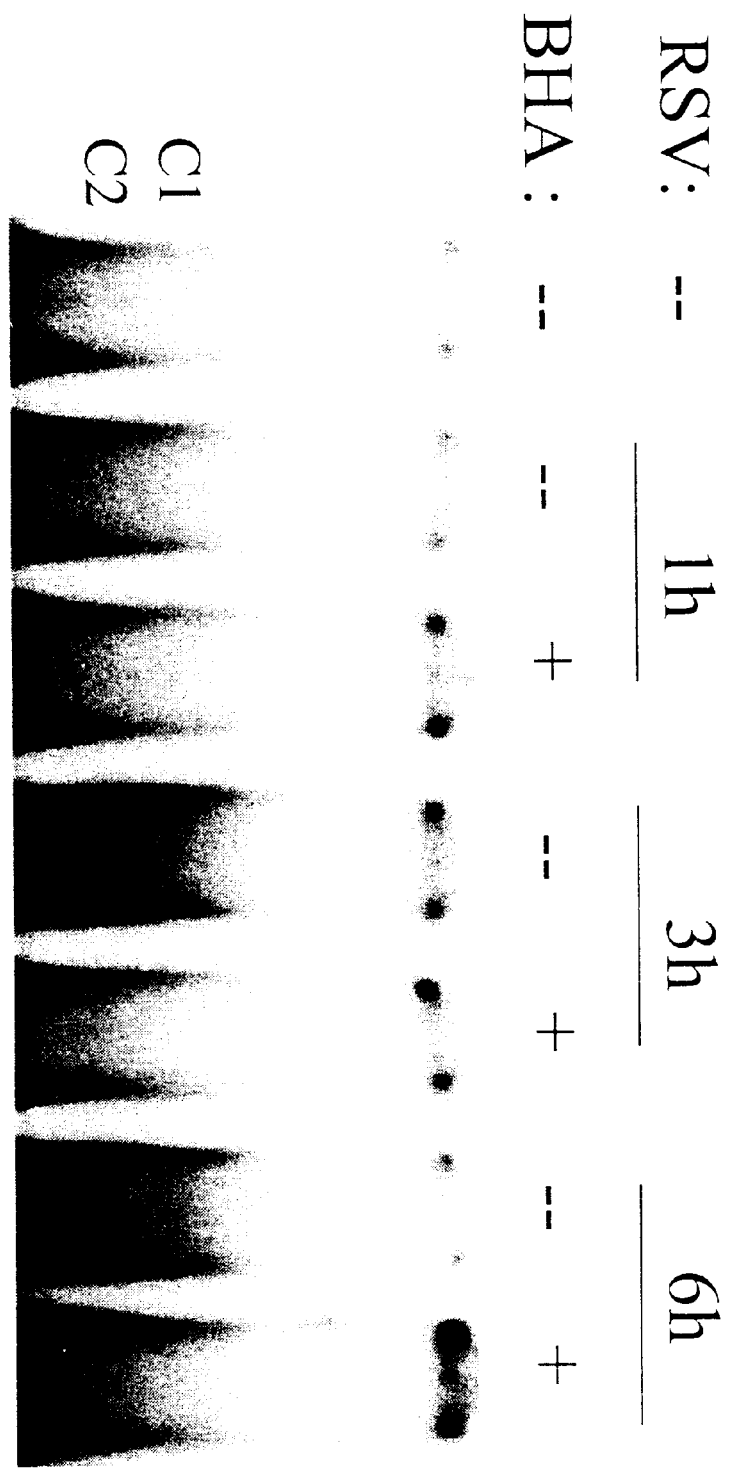

FIG. 16. EMSA of IRF-1 GAS binding complexes in response to antioxidant treatment. Nuclear extracts were prepared from A549 cells control and infected with RSV for various lengths of time, in the absence or presence of 400 μM BHA, and used for binding to the IRF-1 GAS in EMSA. Time (in hours) following RSV infection is indicated at top. Shown are the two nucleoprotein complexes formed on the probe in response to RSV infection.

FIG. 17. EMSA of IRF-7 ISRE binding complexes in response to RSV infection. Panel A: effect of antioxidant treatment. Nuclear extracts were prepared from A549 cells control and infected with RSV for various lengths of time, in the absence or presence of 400 μM BHA, and used for EMSA. Time (in hours) following RSV infection is indicated at top. Panel B: supershift-interference assay. Nuclear extracts of A549 cells infected for 6 hours were used in the EMSA in the presence of preimmune serum (PI), anti-STAT-1, -2, -3, and anti-IRF-1 and -9 antibodies. Arrows indicates supershifted complexes.

Figure 18:
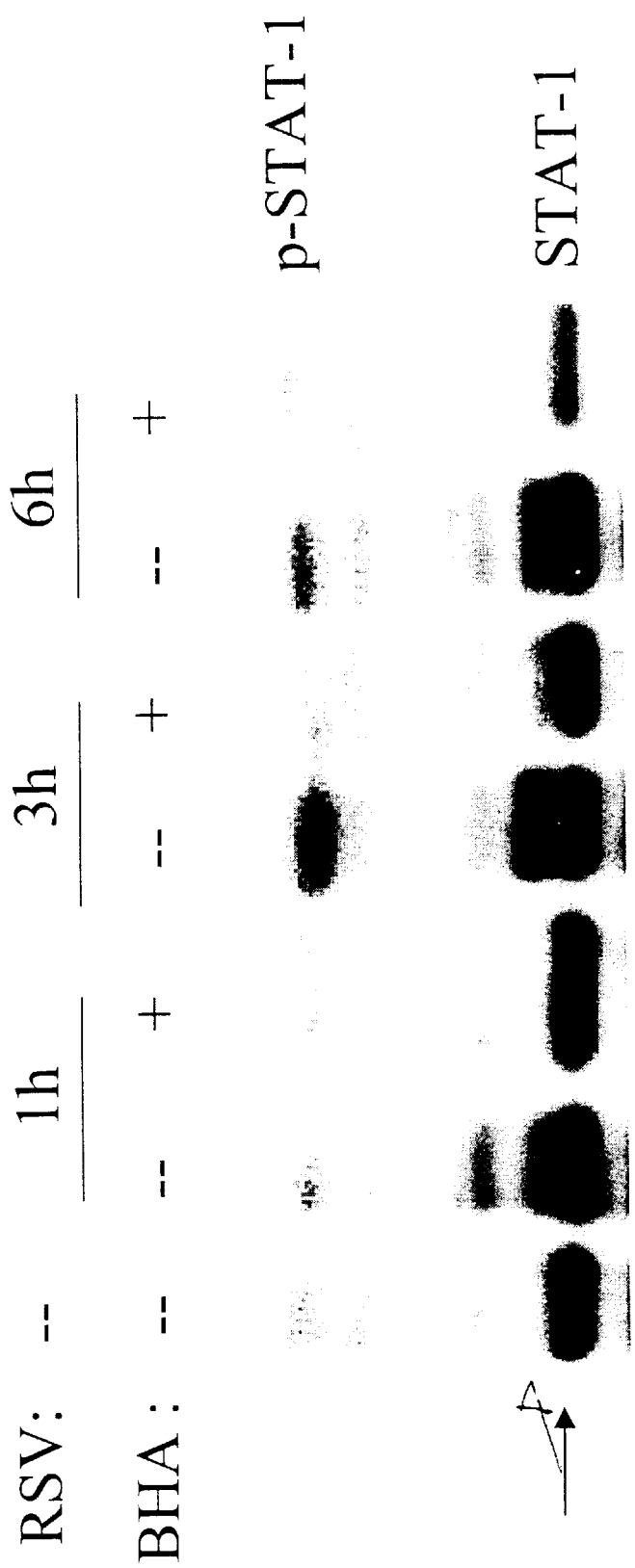

FIG. 18. Effect of BHA on STAT-1 phosphorylation and nuclear abundance. A549 cells were infected with RSV for 1, 3 and 6 hours, in the absence or presence of 400 μM BHA. Cells were harvested to prepare nuclear extracts and equal amounts of protein from control and infected cells were assayed for phosphorylated and total STAT-1 by Western blot. Arrow indicates the inducible STAT-1 form detectable after RSV infection.

FIG. 19. Effect of BHA on STAT-3 phosphorylation and nuclear abundance. Panel A: time course. Nuclear extracts were prepared from A549 cells control and infected with RSV for 3, 6 and 12 hours and assayed for phosphorylated STAT-3 by Western blot. Panel B: effect of BHA. A549 cells were infected with RSV for 3 and 6 hours, in the absence or presence of 400 μM BHA. Cells were harvested to prepare nuclear extracts and equal amounts of protein from control and infected cells were assayed for phosphorylated and total STAT-3 by Western blot.

DETAILED DESCRIPTION OF THE INVENTION

The present invention relates to a method of treating lung inflammation in a subject which includes administering butylated hydroxyanisole to the subject in an amount effective to treat lung inflammation.

As used herein, "treating" lung inflammation is defined as reversing, alleviating, inhibiting the progress of, or preventing the disorder or condition to which such term applies, or one or more symptoms of such disorder or condition.

As used herein, the phrase an "amount effective" and/or a "therapeutically effective amount" means that amount of a compound of the present invention (such as butylated hydroxyanisol) which prevents the onset of, alleviates the symptoms of, or reverses or inhibits the progression of a condition.

As used herein, "subject" is defined as a mammal, such as a human, or a cell culture of a mammal.

RANTES (regulated upon activation, normal T-cells expressed and secreted) is a C—C chemokine with structural similarity to the interleukin-8 (IL-8) and human MIP-1.beta. (Covell D G et al. (1994) Protein Science 3:2064–72). It is expressed by T lymphocytes and macrophages and has been identified in some tumor cell lines and in rheumatoid synovial fibroblasts. Both human and murine forms of the 68 amino acid mature protein are known; they share 85% homology and some cross reactivity. The human gene is located on chromosome 17q11–q21. (Shin H S et al (1994) Mol Cell Biol 14:2914–25). C—C chemokines, including RANTES, are described in U.S. Pat. No. 6,238,666, which is incorporated herein by reference. Human RANTES sequence is published in Schall, et al (1988) J Immunol 141:1018–25.

In the method of the present invention, butylated hydroxyanisol inhibits RANTES gene expression in the subject, particularly in the alveolar cells of the subject. Further, the administration of butylated hydroxyanisole inhibits RANTES protein secretion in the subject, particularly in the alveolar cells in the subject.

Regulation of gene expression can occur at several different levels, but the activation of gene-specific transcription factors is considered the most fundamental to this process. One family of transcription factors, the interferon regulatory factors (IRFs), includes members: IRF-1, IRF-3, and IRF-7. (Veals et al., Mol. Cell. Biol., 12:3315–3324 (1992); Miyamoto et al., Cell, 54:903–913 (1988); Harada et al., Cell, 58:729–739 (1989); Zhang, L. and J. S. Pagano. Mol. Cell. Biol. 17:5748–5757, 1997)). cDNA expression studies have demonstrated that IRF-1 functions as a transcriptional activator of IFN and IFN-inducible genes (Fujita et al., Nature, 337:270–272 (1989); Harada et al., Cell, 63:303–312

(1990). Recent analyses have shown that IRF-1 can also act as a tumor suppressor gene (Harada et al, Science, 259:971–974 1993). IRF-3 controls the production of interferons and chemokines in virus infected cells, by a post-translational mechanism that involves virus induced phosphorylation, protein dimerization, cytoplasmic to nuclear translocation and stimulation of responsive genes (27).

In the method of the present invention the butylated hydroxyanisol inhibits interferon regulatory factor activation. In particular, the butylated hydroxyanisol inhibits IRF-1 gene expression, IRF-7 gene expression, and inhibits IRF-3 nuclear translocation.

In particular, the butylated hydroxyanisol blocks a molecule binding to the gamma interferon activated sequence of IRF-1 where the molecule is STAT-1 or STAT-3. In addition, the butylated hydroxyanisol blocks a molecule binding to the interferon stimulated response element of IRF-7, where the molecule is STAT-2, STAT-1, IRF-1, and/or IRF-9.

In one embodiment of the present invention, the method includes contacting an alveolar cell of the subject with the butylated hydroxyanisol. In one embodiment, the subject is a human.

The butylated hydroxyanisol may be administered alone or in combination with compatible carriers as a composition in the method of the present invention. Compatible carriers include suitable pharmaceutical carriers or diluents. The diluent or carrier ingredients should be selected so that they do not diminish the therapeutic effects of the compounds used in the present invention.

The compositions herein may be made up in any suitable form appropriate for the desired use. Examples of suitable dosage forms include intranasal (such as by spray or aerosol), oral, parenteral, or topical dosage forms.

Suitable dosage forms for oral use include tablets, dispersible powders, granules, capsules, suspensions, syrups, and elixirs. Inert diluents and carriers for tablets include, for example, calcium carbonate, sodium carbonate, lactose, and talc. Tablets may also contain granulating and disintegrating agents, such as starch and alginic acid; binding agents, such as starch, gelatin, and acacia; and lubricating agents, such as magnesium stearate, stearic acid, and talc. Tablets may be uncoated or may be coated by known techniques to delay disintegration and absorption. Inert diluents and carriers which may be used in capsules include, for example, calcium carbonate, calcium phosphate, and kaolin. Suspensions, syrups, and elixirs may contain conventional excipients, for example, methyl cellulose, tragacanth, sodium alginate; wetting agents, such as lecithin and polyoxyethylene stearate; and preservatives, such as ethyl-p-hydroxybenzoate.

Dosage forms suitable for parenteral administration and/or intranasal administration include solutions, suspensions, dispersions, emulsions, and the like. They may also be manufactured in the form of sterile solid compositions which can be dissolved or suspended in sterile medium immediately before use. They may contain suspending or dispersing agents known in the art. Examples of parenteral administration are intraventricular, intracerebral, intramuscular, intravenous, intraperitoneal, rectal, and subcutaneous administration.

In addition to the above generally non-active components of the above-described formulations, these formulations can include other active materials, particularly, actives which have been identified as useful in the treatment of lung inflammation. For example, the other actives can also have anti-inflammatory properties, or, alternatively, they can have no such anti-inflammatory properties.

It will be appreciated that the actual preferred amount of compound to be administered according to the present invention will vary according to the particular compound, the particular composition formulated, and the mode of administration. Many factors that may modify the action of the compound (e.g., body weight, sex, diet, time of administration, route of administration, rate of excretion, condition of the subject, drug combinations, and reaction sensitivities and severities) can be taken into account by those skilled in the art. Administration can be carried out continuously or periodically within the maximum tolerated dose. Optimal administration rates for a given set of conditions can be ascertained by those skilled in the art using conventional dosage administration tests.

Another aspect of the present invention relates to a method of inhibiting interferon regulatory factor activation in a subject which includes administering butylated hydroxyanisol to the subject in an amount effective to inhibit interferon regulatory activation in the subject.

Yet another aspect of the invention relates to a method of inhibiting interferon regulatory factor activation in an alveolar cell which includes contacting the alveolar cell with butylated hydroxyanisol in an amount effective to inhibit interferon regulatory factor activation.

Yet another aspect of the invention relates to a method of measuring inflammation of alveolar cells which includes contacting the alveolar cells with respiratory syncytial virus and measuring the generation of reactive oxygen species in the alveolar cells.

The present invention is further illustrated with the following examples.

EXAMPLES

Example 1

Materials and Methods

RSV preparation. The human Long strain of RSV (A2) was grown in Hep-2 cells and purified by centrifugation on discontinuous sucrose gradients as described elsewhere (15). The virus titer of the purified RSV pools was 8–9 log plaque forming units (PFU)/ml using a methylcellulose plaque assay. No contaminating cytokines were found in these sucrose-purified viral preparations (16). Lipolysaccharide (LPS), assayed using the limulus hemocyanin agglutination assay, was not detected. Virus pools were aliquoted, quick-frozen on dry ice/alcohol and stored at −70° C. until used.

Cell culture and infection of epithelial cells with RSV. A549, human alveolar type II-like epithelial cells (ATCC, Manassas, Va.), were maintained in F12K medium containing 10% (v/v) fetal bovine serum (FBS), 10 mM glutamine, 100 IU/ml penicillin and 100 $\mu$g/ml streptomycin. Small alveolar epithelial cells (SAE) were obtained from Clonetics (San Diego, Calif.) and grown according to the company instructions. Cell monolayers were infected with RSV at multiplicity of infection (MOI) of 1 (unless otherwise stated), as described (17). An equivalent amount of a 20% sucrose solution was added to uninfected A549 cells, as a control. For the antioxidant experiments, cells were pretreated with the antioxidants for one hour and then infected in the presence of the antioxidants. Since BHA was diluted in ethanol, equal amounts of ethanol were added to untreated cells, as a control. Total number of cells, cell viability and viral replication, following antioxidant treatment, were measured by trypan blue exclusion and by plaque assay, respectively.

RANTES ELISA. Immunoreactive RANTES was quantitated by a double antibody ELISA kit (DuoSet, R&D Systems, Minneapolis, Minn.) following the manufacturer's protocol.

Northern Blot. Total RNA was extracted from control and infected A549 cells by the acid guanidium thiocyanate-phenol chloroform method (18). Twenty micrograms of RNA were fractionated on a 1.2% agarose-formaldehyde gel, transferred to nylon membranes and hybridized to a radiolabeled RANTES, IRF-1, -3 and -7 cDNAs, as previously described (19). Hybridization temperature for all probes was 55° C. After washing, membranes were exposed for autoradiography using Kodak XAR film at −70° C. using intensifying screens. After exposure, membranes were stripped and rehybridized with a β-actin probe.

Assesment of intracellular ROS generation. A549 cells were grown in 96-well tissue culture plates and infected with RSV, at 0.1, 0.5 and 1 multiplicity of infection (MOI). At different times post-infection, cells were washed with Hank's Balanced Salt Solution (HBSS) and loaded with 10 $\mu$M 2,7 dichlorofluorescein diacetate (DCF-DA) in HBSS medium containing 25 mM HEPES, pH 7.4, for 30 minutes at 37° C. The cells were then washed twice and fluorescence intensity was determined at 485 nm excitation and 590 nm emission, using an automated fluorescence reader (Flurocount, Hewlett-Packard Instruments, IL). For the experiments in which $H_2O_2$ was used as a stimulus for ROS production, cells were preloaded with 10 M DCF-DA for 30 minutes, washed and then fluorescence intensity was measured at different times following addition of $H_2O_2$. Measurements were performed in triplicate and results expressed as fluorescence mean±S.D. of n=3 independent experiments.

Plasmid construction and cell transfection. A fragment of the human RANTES promoter spanning from −220 to +55 nucleotides (nt), relative to the mRNA start site designated +1 was cloned into the luciferase reporter gene vector pGL2 (Promega, Madison, Wis.) and defined as pGL2-220. Site mutations of the RANTES ISRE in the context of pGL2-220 plasmid were introduced by PCR using the following upstream and downstream mutagenic primers (mutations in lower cases):

SEQ. ID. No.: 1 (5'CATATTTCAGTaaaCTaaaCCGT 3') and
SEQ. ID. No: 2 (3'TATAAAGTCAtttGA ttt GGCAT 5').

Logarithmically growing A549 cells were transfected in triplicate in 60 mm petri dishes by DEAE-Dextran, as previously described (20). Cells were incubated in 2 ml of HEPES buffered Dulbecco's modified Eagle's medium (DMEM) (10 mM Hepes, pH 7.4) containing 20 $\mu$l of 60 mg/ml DEAE-Dextran (Amersham Pharmacia Biotec, Arlington Heights, Ill.) premixed with 6 $\mu$g of RANTES-pGL2 plasmids and 1 $\mu$g cytomegalovirus (CMV)-β galactosidase internal control plasmid. After 3 hours, media was removed and 0.5 ml of 10% (v/v) DMSO in phosphate buffered saline (PBS) was added to the cells for 2 minutes. Cells were washed with PBS and cultured overnight in 10% FBS/DMEM. The next morning, cells were infected with RSV and at 24 hours post-infection cells were lysed to measure independently luciferase and β-galactosidase reporter activity, as previously described (20). Luciferase was normalized to the internal control β-galactosidase activity. All experiments were performed in duplicate or triplicate.

Electrophoretic mobility shift assay (EMSA): Nuclear extracts of uninfected and infected A549 cells were prepared using hypotonic/nonionic detergent lysis, as previously described (20). Proteins were normalized by protein assay (Protein Reagent, Bio-Rad, Hercules, Calif.) and used to bind to a duplex oligonucleotide corresponding to the RANTES ISRE, whose sequences is shown below:

SEQ. ID. No.: 3 (5'GATCCATATTTCAGTTTTCTTTTCCGT 3')
SEQ. ID. No.: 4 (3'TATAAAGTCAAAAGAAAAGGCATCTAG 5')

DNA-binding reactions contained 10–15 $\mu$g nuclear proteins, 5% glycerol, 12 mM HEPES, 80 mM NaCl, 5 mM dithiothreitol (DTT), 5 mM $Mg_2Cl$, 0.5 mM EDTA, 1 $\mu$g of poly dI-dC and 40,000 cpm of $^{32}P$-labeled double-stranded oligonucleotide in a total volume of 20 $\mu$l. The nuclear proteins were incubated with the probe for 15 minutes at room temperature and then fractionated by 6% nondenaturing polyacrylamide gels (PAGE) in TBE buffer (22 mM Tris-HCl, 22 mM boric acid, 0.25 mM EDTA, pH 8). After electrophoretic separation, gels were dried and exposed for autoradiography using Kodak XAR film at −70° C. using intensifying screens.

Microaffinity isolation assay. Microaffinity purification of proteins binding to the RANTES ISRE was performed using a two-step biotinylated DNA-streptavidin capture assay (20). In this assay, duplex oligonucleotides are chemically synthesized containing 5' biotin (Bt) on a flexible linker (Genosys, the Woodlands, TX). Four hundred micrograms of 12 hours-infected A549 cells nuclear extracts were incubated at 4° C. for 30 minutes with 50 pmoles of Bt ISRE, in the absence or presence of 10 fold molar excess of non-biotinylated ISRE wild type (WT) or mutated (MUT). The binding buffer contained 8 $\mu$g poly dI/dC (as nonspecific competitor) and 5% (v/v) glycerol, 12 mM HEPES, 80 mM NaCl, 5 mM DTT, 5 mM $Mg_2Cl$, 0.5 mM EDTA. One hundred $\mu$l of a 50% slurry of pre-washed streptavidin-agarose beads was then added to the sample, and incubated at 4° C. for an additional 20 minutes with gentle rocking. Pellets were washed twice with 500 $\mu$l binding buffer, and the washed pellets were resuspended in 100 $\mu$l 1×SDS-PAGE buffer, boiled and fractionated on a 10% SDS-polyacrylamide gel. After electrophoresis separation, proteins were transferred to polyvinylidene difluoride (PVDF) membrane for Western blot analysis.

Western Immunoblot. Total cell lysates and cytoplasmic and nuclear proteins were prepared as previously described, fractionated by SDS-PAGE and transferred to PVDF membrane (20). Membranes were blocked with 5% albumin in TBS-Tween and incubated overnight with a rabbit polyclonal antibody to IRF-1, -3 and -7 (Santa Cruz Biotech, Santa Cruz, Calif.). For secondary detection, a horseradish-coupled anti-rabbit or anti-mouse antibody was used in the enhanced chemiluminescence assay (Amersham Pharmacia Biotec, Arlington Heights, Ill.).

Statistical Analysis. Data from experiments involving multiple samples subject to each treatment were analyzed by the Student Newman Keuls t-test for multiple pairwise comparisons. Results were considered significantly different at a p value <0.05.

The composition of the cellular response at sites of tissue inflammation is controlled by gradients of chemokines, a family of small chemotactic cytokines, which direct leukocyte transendothelial migration and movement through the extracellular matrix. RANTES is a CC chemokine highly chemoattractant for T lymphocytes, monocytes, eosinophils and basophils (5), all cell types which are present or activated in the inflammatory infiltrate that follows RSV infection of the lung. Recent in vivo studies have shown elevated RANTES concentrations in nasal washes and bronchoalveolar lavages of children infected with RSV (6;7) RANTES is strongly expressed in RSV-infected respiratory epithelial cells (8;9), which are the primary target for viral infection. Therefore, it is likely that RANTES produced by infected epithelial cells plays an important role in the pathogenesis of RSV-induced airway inflammation.

Reactive oxygen species (ROS) are ubiquitous, highly diffusable and reactive molecules produced as a result of reduction of molecular oxygen, including species such as hydrogen peroxide, superoxide anion, and hydroxyl radical, and they have been implicated in damaging cellular components like lipids, proteins and DNA. In the past few years, there has been increased recognition of their role as redox regulators of cellular signaling (10;11). Inducible ROS generation has been shown following stimulation with a variety of molecules, like cytokines and growth factors, and infection with certain viruses, like HIV, Hepatitis B and influenza (12). Changes in the level of ROS, generated in response to some of these stimuli, have been shown to modulate the expression of several genes (10). Among the different members of the chemokine family, interleukin (IL)-8 is the only one for which redox-sensitive signaling pathways have been identified (13;14). The contribution of ROS in RANTES gene expression, as well as in other CC chemokine induction, has not been defined yet. Therefore, the purpose of this example was to investigate the effect of RSV infection on ROS generation in human airway epithelial cells and the role of ROS in RSV-induced RANTES production. Results indicate that RSV infection of airway epithelial cells induces ROS production, as measured by intracellular oxidation of 2', 7'dichlorofluorescein, and that treatment of airway epithelial cells with the antioxidant butylated hydroxyanisol (BHA), as well as a panel of chemically unrelated antioxidants, blocks RSV-induced RANTES protein secretion and gene expression. This effect is mediated through the inhibition of RSV-induced Interferon Regulatory Factor (IRF) binding to the RANTES Interferon Stimulated Responsive Element (ISRE), an event that is absolutely required for RSV-stimulated RANTES gene transcription. In infected A549 cells, ISRE binds IRF-1, -3 and -7. IRF-1 and -7 are inducible upon RSV infection of alveolar epithelial cells and treatment with BHA inhibits their gene expression and protein synthesis. In contrast, IRF-3 is constitutively expressed and antioxidant treatment blocks its nuclear translocation. These data strongly indicate that a redox-sensitive pathway is involved in RSV-induced IRF induction and RANTES gene expression. This example provides novel insights on the role of ROS in viral-induced RANTES secretion and IRF protein activation. Identification of the molecular mechanisms involved in RANTES gene expression is fundamental for developing strategies to modulate the inflammatory response associated with RSV infection of the lung.

Results

RSV Induces Reactive Oxygen Species Formation

To determine whether RSV infection induced ROS production, A549 cells were grown to ~90% of confluency and infected with RSV. At different time points after infection, cells were loaded with the membrane permeable compound 2',7' DCFDA, which is trapped intracellularly following cleavage by cellular esterases. DCF oxidation was measured by changes in mean fluorescence intensity in control vs infected cells (21;22). When cells were infected with MOI of 1, the production of ROS was detectable as early as 2 hours post-infection, reaching a plateau around 4 hours and declining thereafter, although the level of cellular ROS in infected cells was still higher than in control cells at 24 hours post-infection (FIG. 1). When cells were infected with a lower MOI, such as 0.1 and 0.5, the kinetic of ROS production was delayed of a few hours, reaching a plateau between 6 and 8 hours post-infection, reflecting the lower number of cells infected at the earliest time-points.

Antioxidants Block RSV-induced RANTES Secretion

RSV is a potent stimulus for RANTES production in cultured human nasal, bronchial and alveolar epithelial cells (8;9). In all epithelial cell types, synthesis of RANTES required replicating virus and was dose- and time-dependent, with increased steady state levels of RANTES mRNA observed between 6 and 12 hours after infection (8;9). To determine the contribution of RSV-induced ROS generation in RANTES secretion, A549 cells were infected with RSV in the absence or presence of the chemically-unrelated antioxidants dimethylsulphoxide (DMSO), N-acetyl cystein (NAC), tetramethyl thiourea (TMTU) and butylated hydroxyanisol (BHA). In preliminary studies, different concentrations of antioxidants were used to identify the most effective ones in inhibiting RANTES secretion (data not shown). 2% (v/v) DMSO, 20 mM NAC, 20 mM TMTU and 400 $\mu$M BHA were sufficient to significantly block RSV-induced RANTES production, with BHA being the most effective (FIG. 2, Panel A). To confirm these results in a normal cell type, similar experiments were performed in small alveolar epithelial (SAE) cells infected with RSV. SAE cells are derived from the small bronchioli of the lung and they show a similar pattern of RANTES induction, following RSV infection, compared to A549 cells (9). As in A549 cells, the antioxidants TMTU, NAC and BHA significantly reduced RSV-induced RANTES production (FIG. 2, Panel B), suggesting that indeed inducible RANTES secretion is regulated in a redox-sensitive manner. Antioxidant treatment did not significantly affect cell viability or viral replication (data not shown).

Since BHA was the most effective compound in reducing RSV-induced RANTES secretion in both A549 and SAE cells, this antioxidant was selected to perform all the subsequent experiments. To directly confirm the ability of BHA to inhibit ROS, A549 cells were stimulated with 200 $\mu$M $H_2O_2$ in the absence or presence of 400 $\mu$M BHA and the amount of cellular ROS was monitored by oxidation of 2'7' DCF. As shown in FIG. 3, $H_2O_2$ was able to induce a high level of ROS production, which was almost completely inhibited by treatment with BHA. These data indicate that BHA function as a potent antioxidant in airway epithelial cells.

BHA Inhibits RSV-induced RANTES Gene Expression

To determine if the reduction in RSV-induced RANTES secretion by BHA was paralled by changes in steady-state level of RANTES mRNA, A549 cells were infected with RSV for various lengths of time, in the absence or presence of the antioxidant, and total RNA was extracted from control and infected cells for Northern blot analysis. A small increase in RANTES mRNA expression was first detected at 6 hours post-infection, with maximal induction between 12 and 24 hours (FIG. 4). There was no further increase in mRNA levels at later time points (data not shown). Treatment with 400 $\mu$M BHA completely inhibited RSV-induced RANTES mRNA induction at 6 and 12 hours post-infection and greatly reduced it at 24 hours (FIG. 4). This dramatic change was not due to a nonspecific effect since total cell number and viability in the group treated with antioxidant were unchanged (data not shown) and levels of the housekeeping gene β-actin were not systematically reduced compared to untreated cells (FIG. 4).

Inducible RANTES gene expression is controlled at both transcriptional and post-transcriptional levels (23–25). In A549 cells, RSV-induced RANTES promoter activation mirrors the induction of the endogenous RANTES gene mRNA, suggesting that in alveolar epithelial cells RANTES expression, following RSV infection, is controlled mainly at the level of transcription (42). To determine whether the antioxidant effect of BHA influenced RANTES gene transcription, A549 cells were transiently transfected with a construct containing the first 974 nucleotides of the human RANTES promoter linked to the luciferase reporter gene, defined as PGL2-974. This fragment of the promoter contains all the necessary regulatory elements that drive regulated luciferase expression in A549 cells following RSV infection (42). The day after, cells were infected with RSV for 24 hours in the absence or presence of BHA. Similar to what has been observed for mRNA levels, treatment with BHA almost completely abolished RSV-induced luciferase activity (FIG. 5), indicating that the antioxidant effect occurs mainly by interfering with RANTES gene transcription.

Effects of BHA Treatment on RSV-induced Transcription Factor Activation

Recently investigations have studied the promoter cis-regulatory elements and nuclear factors involved in the regulation of RANTES gene transcription following RSV infection of human airway epithelial cells. The results of that study have indicated that RSV-induced RANTES transcription requires cooperation of multiple response elements, including the Interferon Stimulated Responsive Element (ISRE) (42). The ISRE is absolutely required for RSV-induced promoter activation, since its mutation completely blocks RSV-induced luciferase activity (FIG. 6). To determine if BHA-induced inhibition of RANTES transcription was due to changes in the abundance of DNA-binding proteins recognizing the RANTES ISRE, electrophoretic mobility shift assays (EMSA) was performed using nuclear extracts prepared from A549 cells control or infected with RSV for 12 hours, in the absence or presence of BHA. As shown in FIG. 7, RSV infection induced a dramatic increase in ISRE binding, which was completely abolished by treatment with BHA.

The major components of the RSV-induced ISRE binding complex are IRF-1, -3 and -7 (42). It has been previously shown that IRF-7 gene expression and protein synthesis is viral inducible, while IRF-3 is constitutively expressed and translocates to the nucleus when phosphorylated in response to a viral infection (26). RSV infection of A549 cells induces de novo synthesis of IRF-1 (20). To determine if RSV infection of A549 cells induced IRF-7 synthesis and IRF-3 activation, Western blot analysis was performed of cytoplasmic and nuclear proteins extracted from A549 cells uninfected or infected for various lengths of time. As shown in FIG. 8, RSV infection induced de novo synthesis of IRF-7 and its nuclear translocation starting around 12 hours post-infection. By contrast, IRF-3 was constitutively expressed and RSV infection induced its nuclear translocation starting around 6 hours post-infection (FIG. 8). The cytoplamic abundance of IRF-3 was lower at 12 hours post-infection, compared to control cells, likely due to the combined effect of nuclear translocation and cytoplasmic proteosome-mediated degradation of the activated form (27). Antioxidant treatment of RSV-infected alveolar epithelial cells greatly reduced the nuclear abundance of IRF-1 and -7 and one of the two detectable nuclear forms of IRF-3, as shown in FIG. 9.

Since the other RSV-inducible nuclear form of IRF-3 was not affected by BHA treatment, it was questioned if this form was able to bind to the RANTES ISRE. For this purpose, a two step microaffinity isolation/Western blot assay was used. In this assay, biotinylated ISRE was used to bind nuclear extracts of control and 12 hours infected A549 cells (20). ISRE-binding proteins were captured by the addition of streptavidine agarose beads, washed and the presence of bound IRF-3 was detected by Western blot. As shown in FIG. 10, there was little detectable binding of IRF-3 in control nuclear extracts, but its abundance was greatly increased after RSV infection. BHA treatment almost completely abolished IRF-3 binding, indicating that the nuclear form of IRF-3 not inhibitable by antioxidant treatment is not able to bind to and therefore to transactivate the RANTES ISRE.

To determine if the reduction in nuclear abundance of IRF-1, -3 and -7 following antioxidant treatment was due inhibition of IRF gene expression, protein synthesis or nuclear translocation, Western blot analysis was performed of whole cell extracts prepared from control and RSV-infected A549 cells, in the absence or presence of BHA. RSV infection induced a strong increase of IRF-1 and -7 protein expression and it caused a shift in the electrophoretic mobility of one of the three detectable forms of IRF-3, an event likely due to changes in IRF-3 phosphorylation, as it has been previously described in Sendai virus-infected cells (28). BHA treatment almost completely abolished RSV-induced IRF-1 and -7 protein synthesis and IRF-3 mobility shift (FIG. 11).

Since the amount of IRF-1 and -7 protein present in the cell is dependent on their gene expression, Northern blot analysis of IRF-1 and -7 mRNA was performed following RSV infection in the absence or presence of BHA. Both IRF-1 and -7 mRNA accumulation was almost completely blocked by antioxidant treatment at 6 and 12 hours post-infection and significantly reduced at 24 hours (FIG. 12). On the other hand, IRF-3 mRNA level was not increased following RSV infection and was unaffected by the antioxidant treatment (data not shown).

In summary, these results strongly suggest that a redox-sensitive signaling pathways is involved in IRF activation and RANTES gene expression following RSV infection of alveolar epithelial cells.

Discussion

Under normal conditions, airway epithelial cells represent an important interface between the external environment and the host. Upon infection or injury they play an important role in initiating the mucosal immune response by producing soluble factors, like chemokines, a family of small chemotactic cytokines, which are able to recruit and activate leukocytes in a cell-type specific manner (29). The immunomodulatory activity of the airway epithelium is of particular relevance to RSV infection, since the inflammatory response triggered by RSV infection appears to be an essential pathogenic component of RSV-induced lung damage (30). RANTES is a CC chemokine highly chemoattractant for T lymphocytes, monocytes, eosinophils and basophils, all cell types which are present or activated in the inflammatory infiltrate that follows RSV infection of the lung. RANTES concentrations are elevated in nasal washes and bronchoalveolar lavages of children infected with RSV (6;7) and RANTES gene is strongly expressed in RSV-infected respiratory epithelial cells (8;9), suggesting that its production by infected epithelial cells may indeed play an important role in the pathogenesis of RSV-induced airway inflammation.

Free radicals and reactive oxygen species have recently been shown to function as second messengers influencing a variety of molecular and biochemical processes, including expression of a number of genes (10). The results of this study demonstrate that RSV infection of alveolar epithelial cells induces ROS formation and activates a redox-sensitive signaling pathway leading to de novo synthesis of the transcription factors IRF-1 and -7 and IRF-3 nuclear translocation, events that play a fundamental role in viral-induced RANTES gene expression (31). This is the first report of increased ROS production in airway epithelial cells following RSV infection. Data show that the kinetic of ROS generation in infected cells is quite fast and precedes RSV-induced transcription factor activation and increase in RANTES mRNA. Several studies have pointed to the ability of certain viruses, including influenza, Sendai, hepatitis B and HIV, to induce the formation of ROS (12). In most cases, the ROS generation was a consequence of the activation of professional phagocytes like monocytes and polymorpho-nuclear cell, similar to that shown for eosinophils, in which RSV infection can induce superoxide production (32). The relationship between viral-induced ROS production and molecular and biochemical processes occurring in infected cells has been more carefully investigated only for HIV. HIV-induced ROS generation has been linked to gene expression and apoptosis (12), although a role for ROS has also been recently been claimed in influenza-induced transcription factor activation and gene expression (33). Mastronarde et al. (34), showed that antioxidant treatment of infected cells was able to block protein synthesis and mRNA induction of Interleukin-8, a pro-inflammatory chemokine that has been extensively investigated in the past few years, whose activation involves ROS-sensitive signaling pathways (13;14). However, that study did not show directly RSV-induced ROS generation.

Since the first evidence that reactive oxygen species can serve as subcellular messengers in signal transduction pathways leading to modification of gene transcription, there has been an explosion in the number of genes whose expression is influenced by cellular redox changes. To date, there was only one report indicating a possible role of ROS in RANTES gene expression, where antioxidant treatment of mesangial cells stimulated with aggregated immunoglobulins, which can enhance ROS formation, was able to inhibit RANTES mRNA induction (35). However, the mechanism of RANTES inhibition by the antioxidant treatment was not investigated. This example indicates that pretreatment of RSV-infected airway epithelial cells with a panel of chemically unrelated antioxidants can effectively inhibits RANTES secretion, mRNA induction and transcription, confirming the involvement of ROS in RANTES gene expression. Although this example did not identify which species of ROS are specifically induced in alveolar epithelial cells infected with RSV, they probably do not include nitric oxide. Indeed, NO induction by RSV infection was unable to be measured and there were no changes in RSV-induced RANTES secretion in cells treated with the nitric oxide synthase inhibitors L-NMMA or L-NAME (data not shown). Furthermore, a similar result was reported by Mastronarde et al. for RSV-induced IL-8 secretion (34).

IRF transcription factors have been shown to play a fundamental role in the induction of several genes involved in the immune/inflammatory response to viral infections, including Interferon alpha and beta, cytokines like IL-15, adhesion molecules, MHC I molecules and inducible NOS (36). RSV has been shown to predispose to the development of asthma (2) and recurrent episodes of wheezing in asthmatic children are often precipitated by RSV infection.

Increased IRF-1 expression has been recently found in airway epithelial cells of patients with asthma, but not in normal individuals or patients with chronic bronchitis (37). IRF protein binding to the ISRE of RANTES promoter is necessary for viral induction of RANTES transcription and gene expression (31). In alveolar epithelial cells IRF-1, -3 and -7 are present in the DNA-nucleoprotein complex formed on the ISRE following RSV infection and all three are involved in RSV-induced RANTES promoter activation. In this example, it is shown for the first time that the antioxidant treatment interferes with RSV-induced RANTES transcription by inhibition of IRF binding to the ISRE, due its multiple effects including blocking of IRF gene expression, protein synthesis or nuclear translocation. IRF-1 and -7 mRNA and protein levels are clearly increased in A549 cells following RSV infection and greatly decreased by the treatment with BHA. The decrease of IRF-1 and -7 protein synthesis is likely the major mechanism for their reduced nuclear abundance in RSV infected cells treated with BHA. However, it is possible that BHA also affects IRF-1 and -7 phosphorylation, which is important for their nuclear translocation and DNA-binding (36). IRF-1 gene expression is induced by Interferon-gamma and cytokines through the activation of STAT and NF-κB transcription factors (38). Similarly, Interferon-gamma activates IRF-7 gene transcription through an ISRE site that binds members of the STAT family (39). BHA treatment of A549 cells did not affect RSV-induced NF-κB nuclear translocation and DNA-binding (data not shown). Therefore, it is possible that BHA treatment affects RSV-induced STAT activation, leading to inhibition of both IRF-1 and -7 gene expression.

Inhibition of phosphorylation and subsequent nuclear translocation is likely the mechanism by which BHA inhibits RSV-induced IRF-3 activation. IRF-3 gene is constitutively expressed and IRF-3 protein is present in cells in multiple forms due to different levels and sites of its phosphorylation, as recently demonstrated by Servant et al. (28). They have recently shown that IRF-3 exists as two forms in unstimulated cells: form I represents non-phosphorylated IRF-3 and form II a basally phosphorylated form. Infection with Sendai virus, as well as Newcastle Disease and measle viruses, all Paramyxoviruses like RSV, induces the appearance of form III and IV, which represent C-terminal phosphorylation of IRF-3. The latter two forms are able to translocate to the nucleus to induce gene expression. In the case of A549 cells, we were able to detect three forms of IRF-3 in unstimulated cells. Following RSV infection, a fourth band could be detected, which is likely to represent a hyperphosphorylated form II of IRF-3, whose formation was inhibited by antioxidant treatment. This hyperphosphorylated form would migrate to the nucleus to bind RANTES ISRE and would correspond to the nuclear form of IRF-3 which disappears following BHA treatment and therefore is no longer present in the RSV-induced ISRE binding complex, as shown by microaffinity-isolation assay. The signaling pathway leading to IRF-3 activation is currently unknown. Faure et al. have recently shown that IRF-1 was necessary for the NOS-2 in retinal epithelial cells stimulated with LPS/Interferon-γ and that the antioxidant PDTC was able to inhibit NOS-2 induction by interfering with LPS/Interferon-γ-induced IRF-1 activation (40). In the case of NOS-2, ERK and p38 MAP kinases are potential candidates as redox-sensitive signaling molecules involved in IRF-1 activation, since both kinases are important for its gene expression (40), both can be activated by $H_2O_2$ stimulation and both are inhibited by antioxidant treatment (41). However, this may not be the case for RSV-induced IRF activation. In fact, even if there is evidence that ERK is also involved in RSV-induced RANTES secretion, inhibitors of ERK activation do not affect RSV-induced binding to the RANTES. This result is in agreement with the recently published observation by Servant et al., showing that pharmacological inhibitors of both ERK and p38 MAP kinases did not affect IRF-3 activation by Sendai virus infection (28).

In summary, this example indicates that the signaling pathway leading to IRF-1 and -7 protein expression and IRF-3 activation involves one or more redox-sensitive molecules that could be different depending on the stimulus applied. Current studies are in progress to identify those signaling molecules activated by RSV infection and leading to IRF protein induction and activation and RANTES production. Identification of the molecular mechanisms involved in RSV-induced gene expression is fundamental for developing strategies to modulate the inflammatory response associated with RSV infection of the lung.

Example 2

Materials and Methods

RSV preparation. The human Long strain of RSV (A2) was grown in Hep-2 cells and purified by centrifugation on discontinuous sucrose gradients as described elsewhere (15). The virus titer of the purified RSV pools, was 8–9 log plaque forming units (PFU)/ml using a methylcellulose plaque assay. No contaminating cytokines were found in these sucrose-purified viral preparations (16). LPS, assayed using the limulus hemocyanin agglutination assay, was not detected. Virus pools were aliquoted, quick-frozen on dry ice/alcohol and stored at −70° C. until used.

Cell culture and infection of epithelial cells with RSV. A549, human alveolar type II-like epithelial cells (ATCC, Manassas, Va.), were maintained in F12K medium containing 10% (v/v) FBS, 10 mM glutamine, 100 IU/ml penicillin and 100 $\mu$g/ml streptomycin. Cell monolayers were infected with RSV at multiplicity of infection (MOI) of 1 (unless otherwise stated), as described (17). An equivalent amount of a 20% sucrose solution was added to uninfected A549 cells, as a control. For the antioxidant experiments, cells were pretreated with the antioxidants for one hour and then infected in the presence of the antioxidant. Since BHA was diluted in ethanol, equal amounts of ethanol were added to untreated cells, as a control. Total number of cells, cell viability and viral replication, following antioxidant treatment, were measured by trypan blue exclusion and by plaque assay, respectively.

Cell transfection. To investigate IRF-1 and -7 gene transcription, A549 cells were transiently transfected with the IRF-1 or -7 promoter, linked to the luciferase reporter gene. Logarithmically growing A549 cells were transfected in triplicate in 60 mm petri dishes by DEAE-Dextran, as previously described (20). Cells were incubated in 2 ml of HEPES buffered DMEM (10 mM Hepes, pH 7.4) containing 20 $\mu$l of 60 mg/ml DEAE-Dextran (Amersham Pharmacia Biotec, Arlington Heights, Ill.) premixed with 6 $\mu$g of either IRF-1 or -7 plasmids and 1 $\mu$g CMV-$\beta$ galactosidase internal control plasmid. After 3 hours, media was removed and 0.5 ml of 10% (v/v) DMSO in PBS was added to the cells for 2 minutes. Cells were washed with PBS and cultured overnight in 10% FBS/DMEM. The next morning, cells were infected with RSV and cells were lysed at different times post-infectionto measure independently luciferase and galactosidase reporter activity, as previously described (20). Luciferase was normalized to the internal control galactosidase activity. All experiments were performed in duplicate or triplicate.

Electrophoretic mobility shift assay (EMSA): Nuclear extracts of uninfected and infected A549 cells were prepared using hypotonic/nonionic detergent lysis, as previously described (20). Proteins were normalized by protein assay (Protein Reagent, Bio-Rad, Hercules, Calif.) and used to bind to a duplex oligonucleotide corresponding to the IRF-1 gamma interferon activated sequence (GAS) and IRF-7 ISRE, whose sequences are shown below.

IRF-1 GAS:
SEQ. ID. No.: 5 5'GATCCAGCCTGATTTCCCCGAAAT-GACGGC 3'
SEQ. ID. No.: 6 3'CGGACTAAAGGGGCTTTACTGC-CGCTCTAG 5'
IRF-7 ISRE
SEQ. ID. No.: 7 5'TTTAGGTTTCGCTTTCCCGGG 3'
SEQ. ID. No.: 8 3'TCCAAAGCGAAAGGGCCCTCG 5'

DNA-binding reactions contained 10–15 $\mu$g nuclear proteins, 5% glycerol, 12 mM HEPES, 80 mM NaCl, 5 mM DTT, 5 mM $Mg_2Cl$, 0.5 mM EDTA, 1 $\mu$g of poly dI-dC and 40,000 cpm of $^{32}P$-labeled double-stranded oligonucleotide in a total volume of 20 $\mu$l. The nuclear proteins were incubated with the probe for 15 minutes at room temperature and then fractionated by 4% nondenaturing polyacrylamide gels (PAGE) in 0.5× TBE buffer (22 mM Tris-HCl, 22 mM boric acid, 0.25 MM EDTA, pH 8), at 120 volts. After electrophoretic separation, gels were dried and exposed for autoradiography using Kodak XAR film at −70° C. using intensifying screens. In the gel mobility supershift, commercial antibodies against specific transcription factors were added to the binding reactions and incubated on ice for one hour prior to fractionation on 6% PAGE.

Western Immunoblot. Nuclear proteins were prepared as previously described, fractionated by SDS-PAGE and transferred to PVDF membrane (20). Membranes were blocked with 5% albumin in TBS-Tween and incubated overnight with antibody recognizing the tyrosine phosphorylated form of STAT-1 and STAT-3 (Santa Cruz Biotech, Santa Cruz, Calif.). Membranes were stripped and reprobed with antibodies to STAT-1 and STAT-3 (Santa Cruz Biotech, Santa Cruz, Calif.). For secondary detection, a horseradish-coupled anti-rabbit or anti-mouse antibody was used (Santa Cruz Biotech, Santa Cruz, Calif.) in the enhanced chemiluminescence assay (Amersham Life Science, Arlington Heights, Ill.).

Though the mechanisms of RSV-induced airway disease and the associated long-term consequences are largely unknown, the local inflammatory response is thought to play a fundamental role. Airway epithelial cell are the target of RSV infection and they respond to the infection producing a variety of mediators involved in lung immune/inflammatory responses, like cytokines, chemokines, interferons, and upregulating adhesion molecules and MHC antigens on the cell surface. Regulation of cellular responses to extracellular stimuli is a central aspect of host defense and it is coordinated by genetic regulatory networks in which different subsets of transcription factors are involved in the expression of diverse set of target genes, depending on the nature of the cellular stimulus. RSV induces gene expression through the coordinate induction of multiple transcription factors that assemble in "enhanceosomes", as was demonstrated for IL-8 and RANTES. The cellular signaling events leading to RSV-induced transcription factor activation are mostly unknown. Reactive oxygen species (ROS) are ubiquitous, highly diffusable and reactive molecules produced as a result of reduction of molecular oxygen, including species such as hydrogen peroxide, superoxide anion, and hydroxyl radical, and they have been implicated in damaging cellular components like lipids, proteins and DNA. In the past few years, there has been increased recognition of their role as redox regulators of cellular signaling (10;11)]. RSV infection of airway epithelial cells rapidly induces ROS production. Pretreatment of airway epithelial cells with the antioxidant butylated hydroxyanisol (BHA), as well a panel of chemically unrelated antioxidants, blocked RSV-induced chemokine gene expression and protein secretion, through inhibition of Interferon Regulatory Factor (IRF) activation. Antioxidant treatment inhibited de novo IRF-1 and -7 genes expression and protein synthesis, and IRF-3 nuclear translocation, indicating that a redox-sensitive pathway was involved in RSV-induced IRF activation. The purpose of this example was to investigate the mechanism of antioxidant modulation of RSV-induced IRF gene expression in human airway epithelial cells. Results indicate that RSV infection of alveolar epithelial cells induces IRF-1 and -7 gene transcription, which is abrogated by treatment with BHA. RSV infection induces binding to the IRF-1 gamma interferon activated sequence (GAS) and the IRF-7 Interferon Stimulated Responsive Element (ISRE) of transcription factors belonging to the Signal Transducers and Activators of Transcription (STAT) family. STAT-1 and STAT-3 bind IRF-1 GAS while STAT-1, STAT-2, IRF-1 and IRF-9 bind IRF-7 ISRE. Antioxidant treatment blocks RSV-induced STAT binding to both IRF-1 GAS and IRF-7 ISRE and inhibits RSV-induced STAT-1 and -3 phosphorylation and nuclear translocation. These data suggest that RSV-induced ROS formation is involved in STAT activation and IRF gene expression, following RSV infection. Treatment of alveolar epithelial cells with a NADPH oxydase inhibitor, (DPI), greatly reduces (or abolishes) STAT activation, indicating that ROS generation, following RSV infection, involves the NADPH oxydase system. This example provides novel insights on the role of ROS in viral-induced IRF and STAT protein activation. Identification of the molecular mechanisms involved in RSV-induced transcription factor activation is fundamental for developing strategies to modulate the inflammatory response associated with RSV infection of the lung.

Results

BHA Inhibits RSV-induced IRF Transcription

Figure 13A:
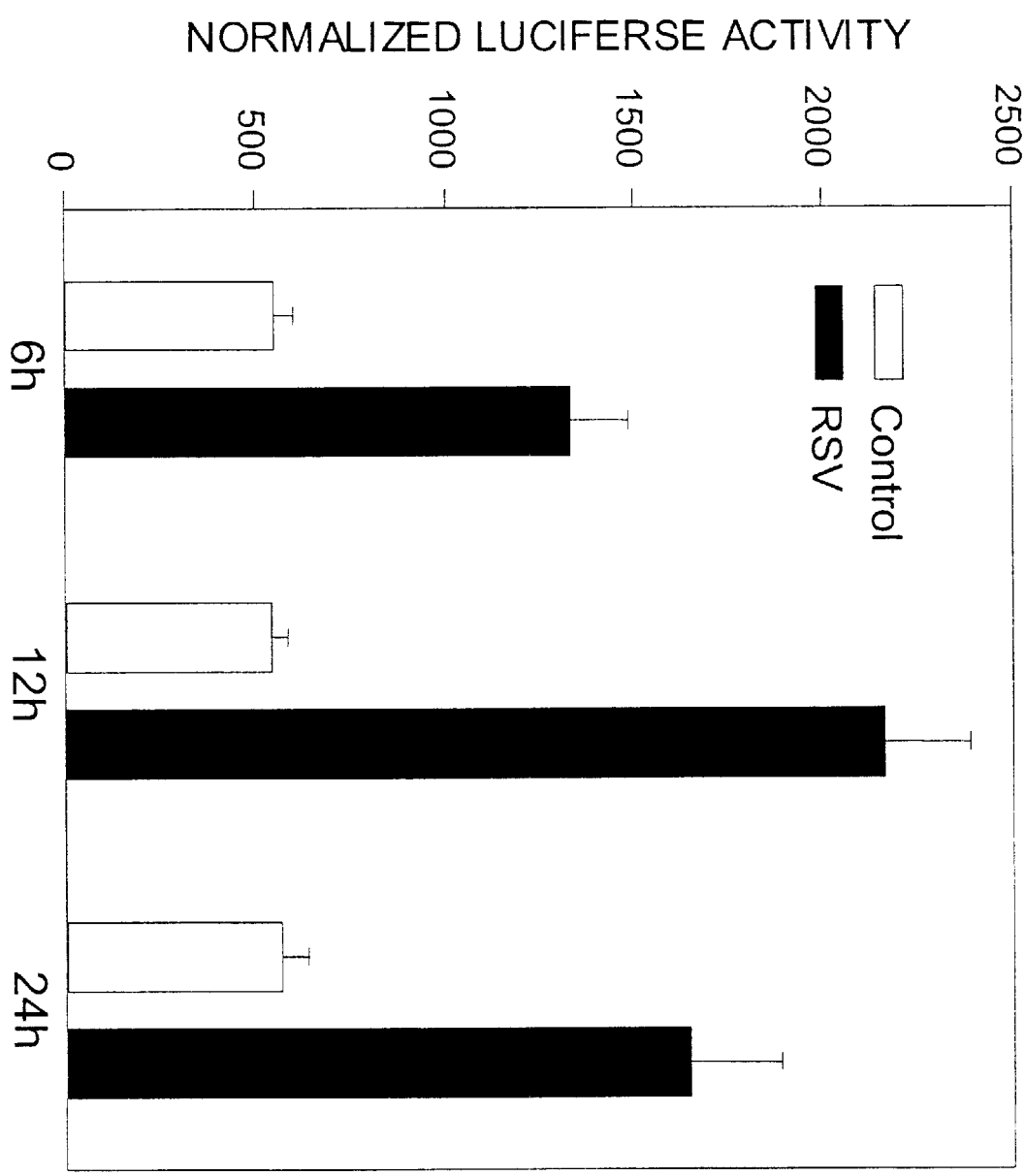
Figure 13B:
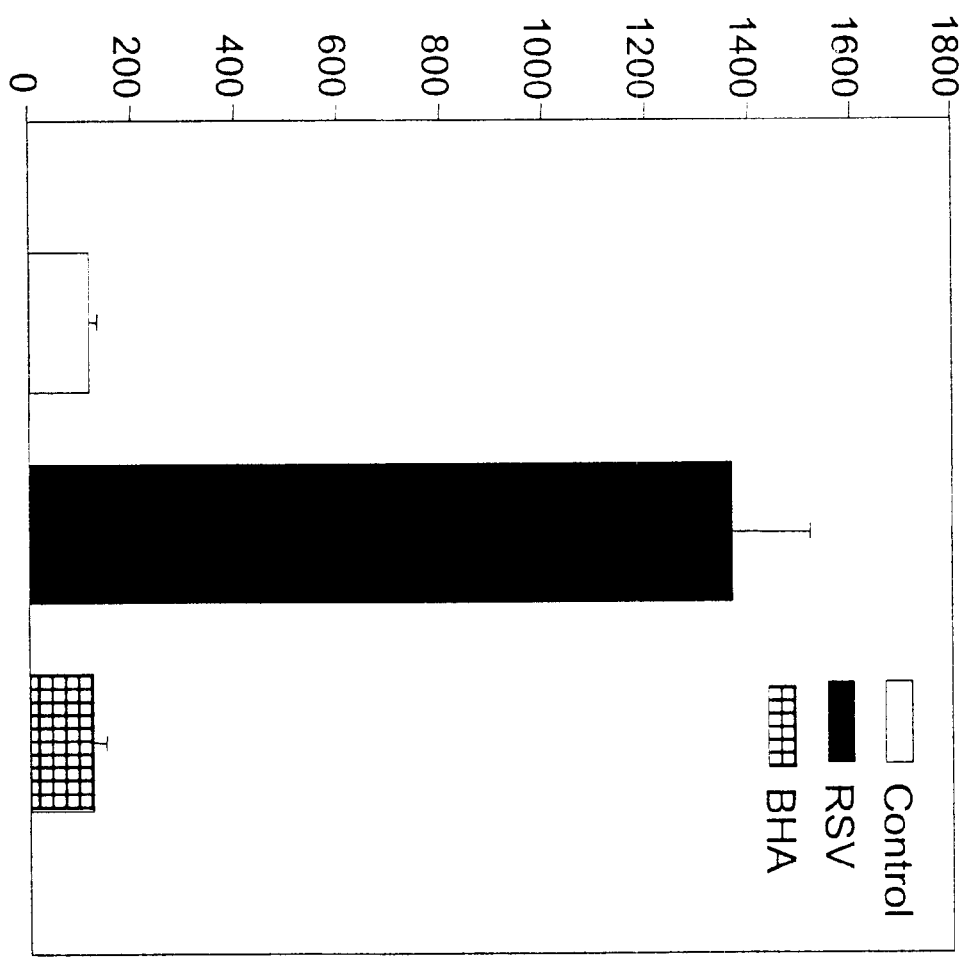

RSV infection of A549 cells, type II-like alveolar epithelial cells, induced IRF-1 and -7 gene expression and antioxidant treatment greatly diminished RSV-induced steady-state IRF mRNA levels. Previous studies, investigating interferon-β and -γ stimulation of IRF-1 and -7 gene induction, have demonstrated that IRF gene expression is controlled, at least in part, at the transcriptional level (38) (39). To determine if IRF-1 gene transcription was increased following RSV infection, A549 cells were transiently transfected with a construct containing the first 1.3 kilobases of the human IRF-1 promoter linked to the luciferase reporter gene (38). The day after, cells were infected with RSV for various length of time and harvested to measure luciferase activity. As shown in FIG. 13A, RSV infection induced a time-dependent increase in IRF-1 promoter activation, which started at 6 hours post-infection, peaked at 12 hours and started to decrease at 24 hours. To determine whether the antioxidant effect of BHA influenced IRF gene transcription, A549 cells were transfected with the IRF-1 promoter, infected with RSV in the absence or presence of BHA and harvested 12 hours later to measure luciferase activity. As shown in FIG. 13B, treatment with BHA completely abolished RSV-induced luciferase activity, suggesting that antioxidant inhibition of IRF-1 gene expression occurs, at least partially, by interfering with gene transcription.

Figure 14A:
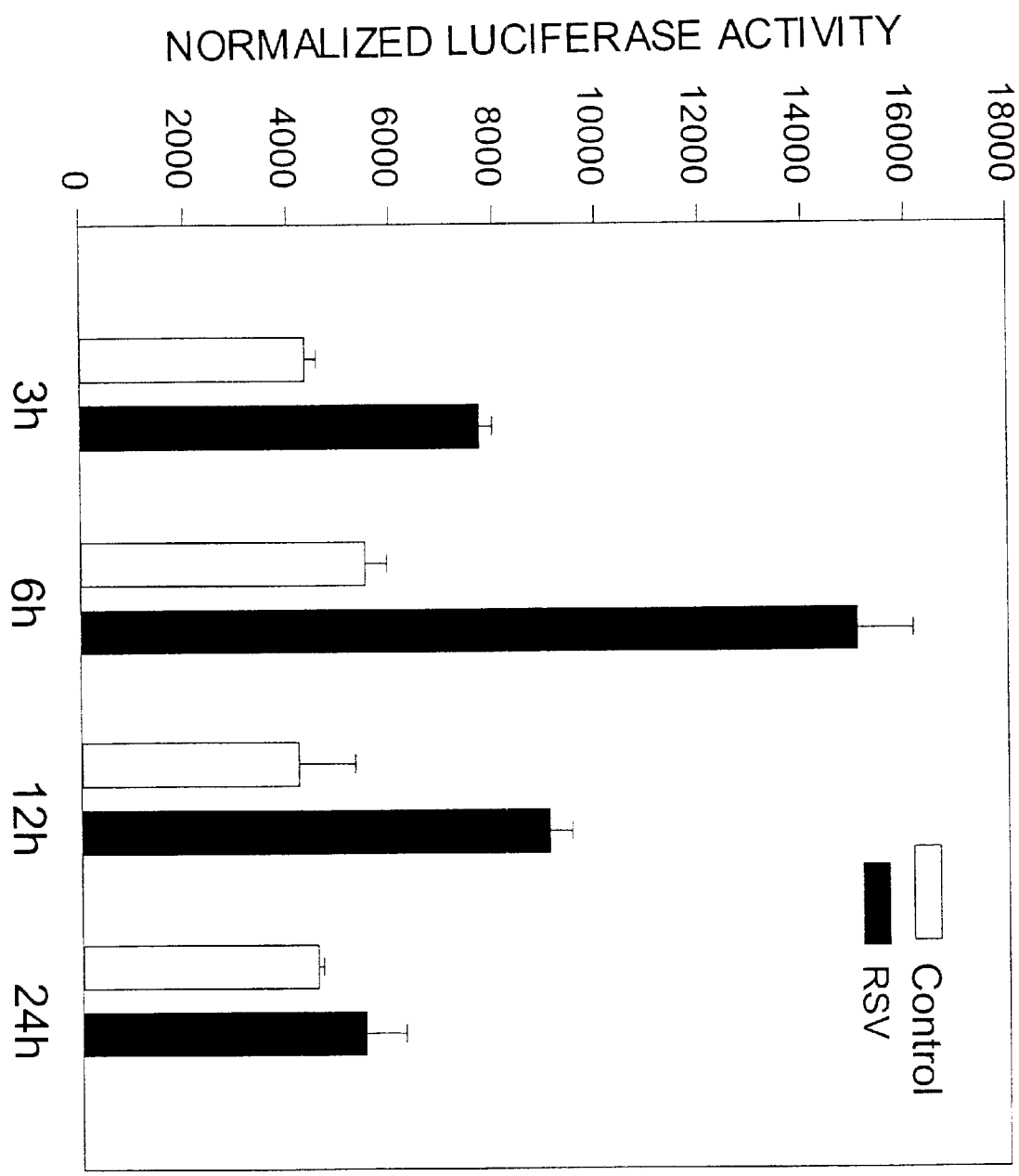
Figure 14B:
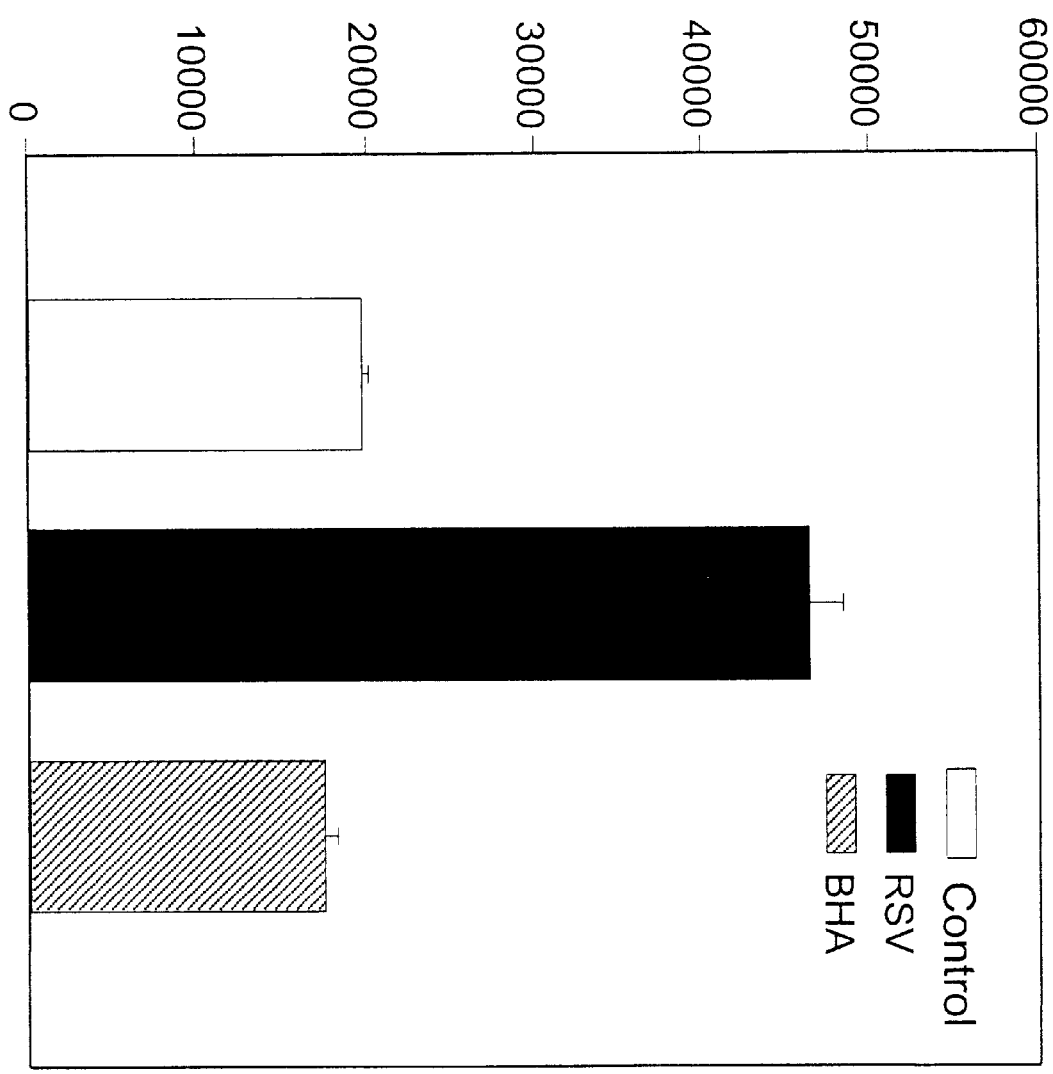

To investigate IRF-7 gene transcription following RSV infection, similar studies were performed using A549 cells transiently transfected with a construct containing the first 1.7 kilobases of the human IRF-7 promoter linked to the luciferase reporter gene (39). As for IRF-1, RSV infection induced a time-dependent increase in luciferase activity, which started around 3 hours post-infection, peaked at 6 hours and returned to almost control levels by 24 hours (FIG. 14A). Similar to IRF-1 promoter activation, BHA treatment completely abolished RSV-induced luciferase activity, indicating that antioxidant treatment inhibits IRF-7 gene transcription (FIG. 14B). It is important to notice that, although BHA treatment inhibited both RSV-induced IRF-1 and -7 promoter activation, it did not affect basal level of transcription of both genes, indicating that BHA does not affect gene transcription in general. BHA does not affect expression of constitutively transcribed cellular genes, like β-actin.

RSV-induced STAT Activation is Redox-sensitive.

Figure 15A:
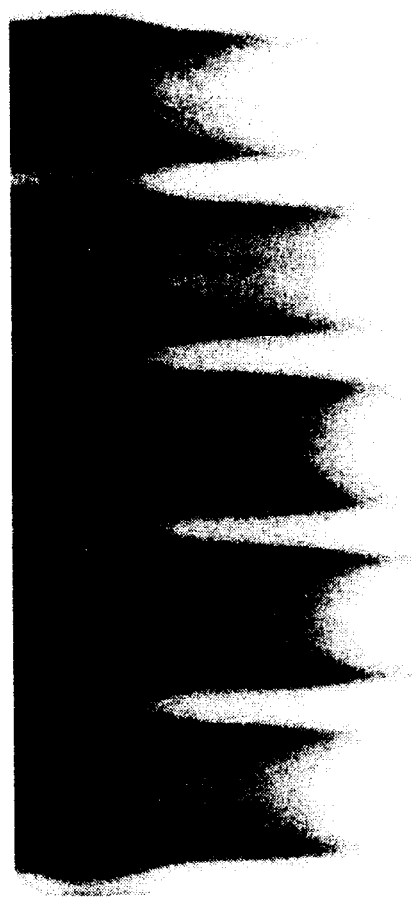
Figure 15B:
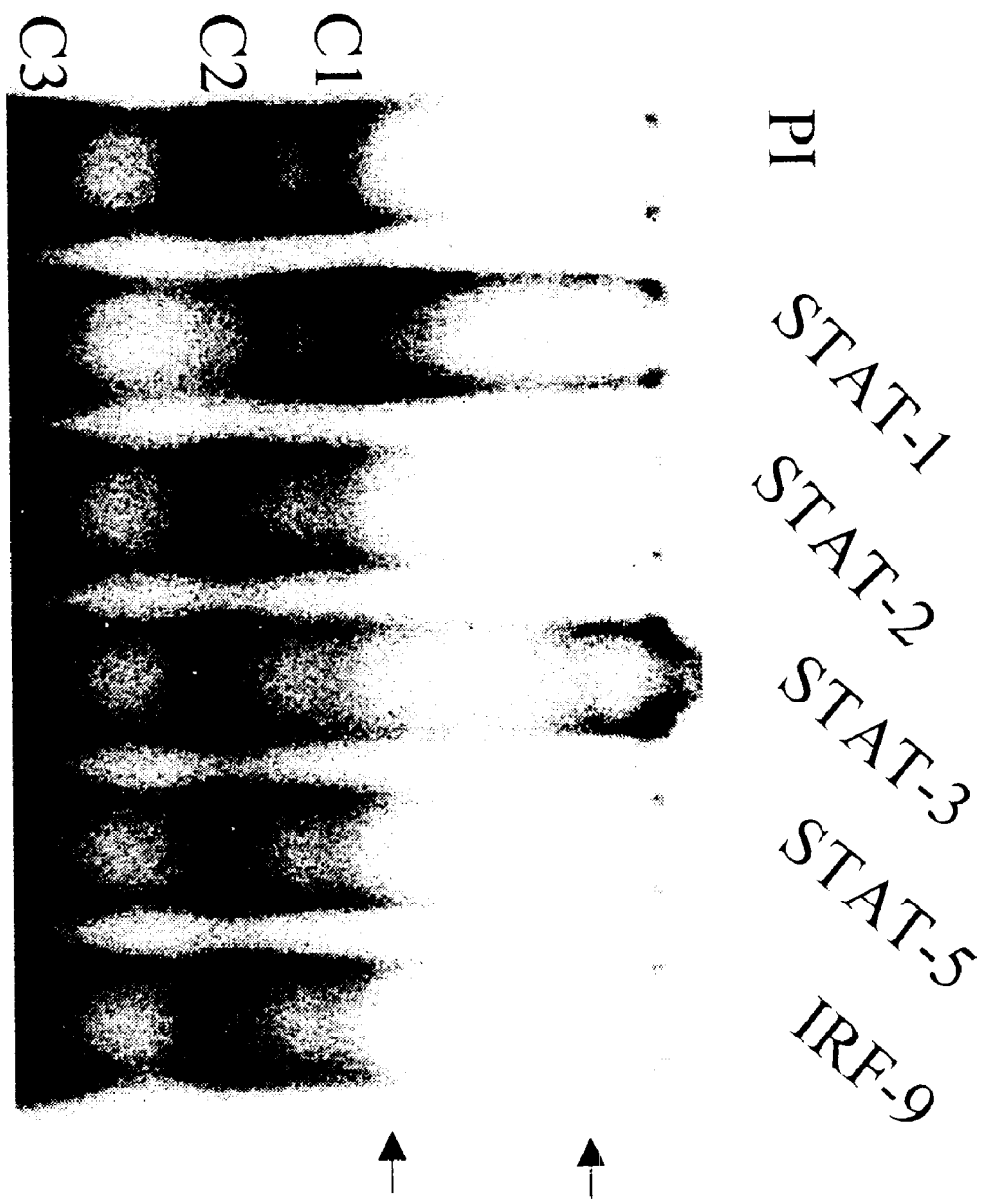

Several studies have investigated the promoter cis-regulatory elements involved in the regulation of IRF-1 gene transcription and the results of those studies have indicated that IRF-1 GAS is a major site necessary for inducible IRF-1 gene transcription. To determine whether RSV infection produced changes in the abundance of DNA-binding proteins recognizing the IRF-1 GAS, electrophoretic mobility shift assays (EMSA) were performed on nuclear extracts prepared from A549 cells control and infected with RSV for various lengths of time. As shown in FIG. 15A, a single nucleoprotein complex (C3) was formed from nuclear extracts of control cells on the IRF-1 GAS probe. RSV infection induced the appearance of two other complexes, C1 and C2, starting between 1 and 3 hours post-infection and a decline after 12 hours of infection. IRF-1 GAS has been shown to bind transcription factors of the STAT family. To determine the composition of the RSV-inducible complexes, supershift assays were performed using a panel of antibodies reacting with the different members of STAT family of transcription factors. The anti-STAT-1 antibody induced the disappearance of C2 and the appearance of a supershifted band, while the anti-STAT-3 antibody caused a reduction of C1 and the appearance of a supershifted band (supershifted complexes are indicated by the arrows), as shown in FIG. 15B. Antibody recognizing STAT-2, STAT-5 and IRF-9 did not induce changes in binding or mobility shifts. These data indicate that STAT-1 and -3 are the major components of the RSV-inducible IRF-1 GAS complexes.

To determine if BHA-induced inhibition of IRF-1 gene transcription was due to changes in STAT binding to the IRF-1 GAS, EMSA was performed using nuclear extracts prepared from A549 cells control or infected with RSV for 6 hours, in the absence or presence of BHA. As shown in FIG. 16, RSV infection induced a dramatic increase in STAT binding, which was completely abolished by treatment with BHA.

Figure 17A:
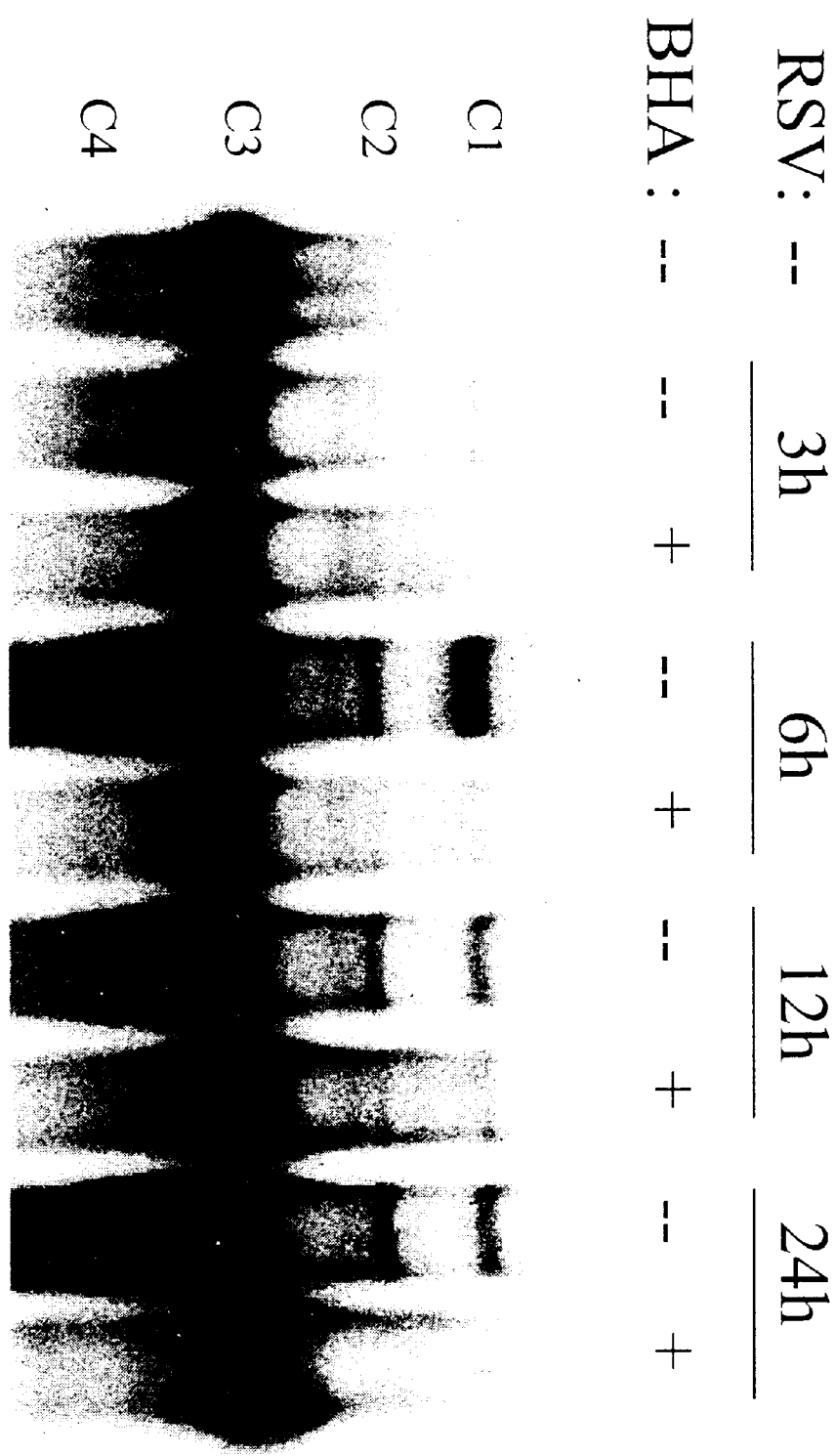
Figure 17B:
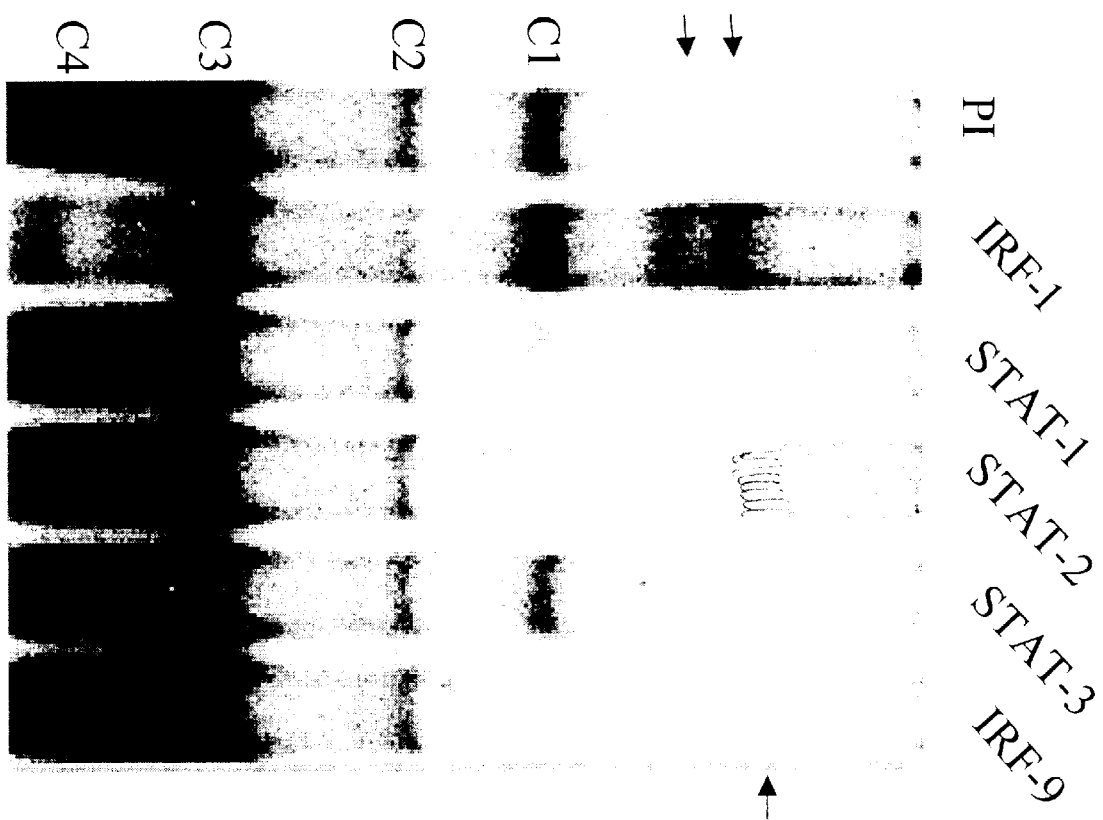

IRF-7 gene transcription is controlled mainly through activation of the promoter ISRE site, which binds transcription factors of the STAT and IRF families. To determine if inhibition of RSV-induced IRF-7 transcription by antioxidant treatment was also due to changes in abundance of proteins binding to the IRF-7 ISRE, EMSA was performed using nuclear extracts of A549 cells control and infected with RSV for various lengths of time, in the presence or absence of BHA. As shown in FIG. 17A, a single nucleoprotein complex (C3) was formed from nuclear extracts of control cells on the IRF-7 ISRE probe. RSV infection induced the appearance of three other complexes, C1, C2 and C3, starting around 3 hours post-infection, with a progressive increase in binding intensity of at 6 hours and a decline after 24 hours of infection. Antioxidant treatment greatly reduced binding of the RSV-inducible complexes to the ISRE probe at all time points. Supershift assays that anti-IRF-1 antibody induced a reduction of C4 and appearance of supershifted bands (indicated by the arrows), while the anti-STAT-1, -2 and IRF-9 antibodies caused the disappearance or reduction of C1 and, in case of anti-STAT-2, the appearance of a faint supershifted band, as shown in FIG. 17B. These data indicate that IRF-1is the major component of the RSV-inducible C4 and STAT-1, STAT-2 and IRF-9, which together form the ISGF3 complex, are the major components of C1. The composition of C2 was not identified.

Figure 19A:
Figure 19B:
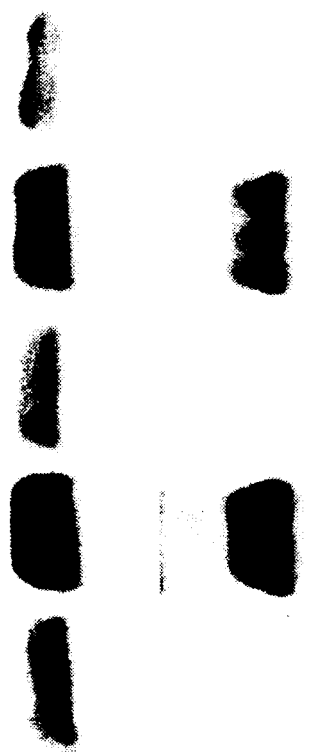

STAT proteins are constitutively expressed and, in unstimulated cells, are located in the cytoplasm. Upon activation, they are phosphorylated on specific tyrosine residues, event necessary for nuclear translocation and dimerization, both required for DNA binding. To determine if inhibition of RSV-induced STAT binding to the IRF-1 GAS, following antioxidant treatment, was due to inhibition of STAT phosphorylation, Western blot analysis was performed of nuclear proteins extracted from A549 cells uninfected or infected for various lengths of time, in the presence or absence of BHA, using anti-STAT-1 and anti-STAT-3 phosphotyrosine specific antibodies. As shown in FIG. 18, RSV infection induced STAT-1 phosphorylation, which was completely blocked by BHA treatment. The same blot was stripped and reprobed with an anti-STAT-1 antibody, showing two forms of nuclear STAT. The first is present in uninfected and infected cells and is not affected by antioxidant treatment; the second form (indicated by the arrow) is RSV-inducible and disappears following BHA treatment, likely representing the tyrosine-phosphorylated STAT-1. RSV infection also induced a time-dependent increase in the abundance of nuclear phosphorylated STAT-3, as shown in FIG. 19A. Antioxidant treatment completely abolished RSV-induce STAT-3 phosphorylation, as shown in FIG. 19B. The same blot was stripped and reprobed with an anti-STAT-3 antibody, showing that RSV-induced STAT-3 nuclear translocation was also completely inhibited by BHA treatment.

Discussion

IRF-1 gene expression is induced by Interferon-gamma and cytokines through the activation of STAT and NF-κB transcription factors (38). Similarly, Interferon-gamma activates IRF-7 gene transcription through an ISRE site that binds members of the STAT family (39). BHA treatment of A549 cells did not affect RSV-induced NF-κB nuclear translocation and DNA-binding (data not shown). Therefore, it is possible that BHA treatment affects RSV-induced STAT activation, leading to inhibition of both IRF-1 and -7 gene expression.

Free radicals and reactive oxygen species have recently been shown to function as second messengers influencing a variety of molecular and biochemical processes, including expression of a number of genes (10).

The relationship between viral-induced ROS production and molecular and biochemical processes occurring in infected cells has been more carefully investigated only for HIV. HIV-induced ROS generation has been linked to gene expression and apoptosis (12), although a role for ROS has also been recently been claimed in influenza-induced transcription factor activation and gene expression (33).

In summary, this example indicates that the signaling pathway leading to IRF-1 and -7 protein expression and IRF-3 activation involves one or more redox-sensitive molecules that could be different depending on the stimulus applied. Current studies are in progress to identify those signaling molecules activated by RSV infection and leading to IRF protein induction and activation and RANTES production. Identification of the molecular mechanisms involved in RSV-induced gene expression is fundamental for developing strategies to modulate the inflammatory response associated with RSV infection of the lung.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

References

1 Hall, C. B. and McCarthy, C. A. (1995) Respiratory Syncytial Virus. In Mandel, G. L., Bennett, J. E., and Dolin, R., editors. *Principles and practice of infectious diseases*, Churchill Livingston, N.Y.

2 Webb, MS. C., Henry, R. L., and Milner, A. D. (1985) *Arch.Dis.Child* 60, 1064–1067

3 Garofalo, R. P., Welliver, R. C., and Ogra, P. L. (1991) *Pediatr.Allergy Immunol.* 2, 30–37

4 Garofalo, R. P., Kimpen, J. L. L., Welliver, R. C., and Ogra, P. L. (1992) *J. Pediatrics* 120, 28–32

5 Alam, R., Stafford, S., Forsythe, P., Harrison, R., Faubion, D., Lett-Brown, M. A., and Grant, J. A. (1993) *J Immunol* 150, 3442–3448

6 Teran, L. M., Seminario, M. C., Shute, J. K., Papi, A., Compton, S. J., Low, J. L., Gleich, G. J., and Johnston, S. L. (1999) *J Infect Dis* 179, 677–681

7 Sheeran, P., Jafri, H., Carubelli, C., Saavedra, J., Johnson, C., Krisher, K., Sanchez, P. J., and Ramilio, m. O. (1999) *Pediatrics Infectious Diseases Journal* 18, 115–122

8 Saito, T., Deskin, R. W., Casola, A., Haeberle, H., Olszewska, B., Ernst, P. B., Alam, R., Ogra, P. L., and Garofalo, R. (1997) *J Infect Dis* 175, 497–504

9 Olszewska-Pazdrak, B., Casola, A., Saito, T., Alam, R., Crowe, S. E., Mei, F., Ogra, P. L., and Garofalo, R. P. (1998) *J Virol* 72, 4756–4764

10 Allen, R. G. and Tresini, M. (2000) *Free Rad Biol Med* 28, 463–499

11 Prasad Gabbita, S., Robinson, K. A., Stewart, C. A., Floyd, R. A., and Hensley, K. (2000) *Arch Biochem & Biophysics* 376, 1–136

12 Schwarz, K. B. (1996) *Free Rad Biol & Med* 21, 641–649

13 Simeonova, P. P., Leonard, S., Flood, L., Shi, X., and Luster, M. I. (1999) *Lab Invest* 79, 1027–1037

14 DeForge, L. E., Preston, A. M., Takeuchi, E., Kenney, J., Boxer, L. A., and Remick, D. G. (1993) *J.Biol.Chem.* 268, 25568–25576

15 Ueba, O. (1978) *Acta.Med.Okayama* 32, 265–272

16 Patel, J. A., Kunimoto, M., Sim, T. C., Garofalo, R., Eliott, T., Baron, S., Ruuskanen, O., Chonmaitree, T., Ogra, P. L., and Schmalstieg, F. (1995) *Am.J.Resp.Cell Mol.* 13, 602–609

17 Garofalo, R. P., Sabry, M., Jamaluddin, M., Yu, R. K., Casola, A., Ogra, P. L., and Brasier, A. R. (1996) *J Virol* 70, 8773–8781

18 Salkind, A. R., Nichols, J. E., and Roberts Jr., N. J. (1991) *J Clin Invest* 88, 505–511

19 Brasier, A. R., Jamaluddin, M., Casola, A., Duan, W., Shen, Q., and Garofalo, R. P. (1998) *J.Biol.Chem.* 273, 3551–3561
20 Casola, A., Garofalo, R. P., Jamaluddin, M., Vlahopoulos, S., and Brasier, A. R. (2000) *J.Immunol.* 164, 5944–5951
21 Kooy, N. W., Royall, J. A., and Ischiropoulos, H. (1997) *Free Rad Res* 27, 245–254
22 Marchesi, E., Rota, C., Fann, Y. C., Chignell, C. F., and Mason, R. P. (1999) *Free Rad Biol & Med* 26, 148–161
23 Koga, T., Sardina, E., Tidwell, R. M., Pelletier, M., Look, D. C., and Holtman, M. J. (1999) *Proc Natl Acad Sci USA* 96, 5680–5685
24 Nelson, P. J., Kim, H. T., Manning, W. c., Goralski, T. J., and Krensky, A. M. (1993) *J Immunol* 151, 2601–2612
25 Boehlk, S., Fessele, S., Mojaat, A., Miyamoto, N. G., Werner, T., Nelson, E. L., Schlondorff, D., and Nelson, P. J. (2000) *Eur J Immunol* 30, 1102–1112
26 Hiscott, J., Pitha, P., Genin, P., Nguyen, H., Heylbroeck, C., Mamane, Y., Algarte, M., and Lin, R. (1999) *J Interferon Cytokine Res* 19, 1–13
27 Lin, R., Heylbroeck, C., Pitha, P. M., and Hiscott, J. (1998) *Mol Cellular Biol* 18, 2986–2996
28 Servant, M. J., ten Oever, B., LePage, C., Conti, L., Gessani, S., Julkunen, I., Lin, R., and Hiscott, J. (2000) *J.Biol.Chem.*
29 Miller, M. D. and Krangel, M. S. (1992) *Critical Reviews in Immunology* 12, 17–46
30 Aherne, W. T., Bird, T., Court, S. D. B., Gardner, P. S., and McQuillin, J. (1970) *J.Clin.Path.* 23, 7–18
31 Lin, R., Heylbroeck, C., Genin, P., Pitha, P. M., and Hiscott, J. (1999) *Molec Cellular Biol* 19, 959–966
32 Kimpen, J. L., Garofalo, R. P., Welliver, R. C., and Ogra, P. L. (1992) *Pediatr.Res.* 32, 160–164
33 Flory, E., Kunz, M., Scheller, C., Jassoy, C., Stauber, R., Rapp, U. R., and Ludwig, S. (2000) *J Biol Chem* 275, 8307–8314
34 Mastronarde, J. G., Monick, M. M., and Hunninghake, G. W. (1995) *Am J Respir Cell Mol Biol* 13, 237–244
35 Satriano, J. A., Banas, B., Luckow, B., Nelson, P., and Schlondorff, D. O. (1997) *J Am Soc Nephrol* 8, 596–603
36 Nguyen, H., Hiscott, J., and Pithas, P. M. (1997) *Cytokine & Growth Editor Review* 4, 293–312
37 Sampath, D., Castro, M., Look, D. C., and Holtzman, M. J. (1999) *J Clin Invest* 103, 1353–1361
38 Harada, H., Takahashi, E., Itoh, S., Harada, K., Hori, T. A., and Taniguchi, T. (1994) *Mol.Cell Biol.* 14, 1500–1509
39 Lu, R., Au, W. C., Yeow, W. S., Hageman, N., and Pitha, P. M. (2000) *J Biol Chem*
40 Faure, V., Hecquet, C., Courtois, Y., and Goureau, O. (1999) *J Biol Chem* 274, 4794–4800
41 Adler, V., Yin, Z., Tew, K. D., and Ronai, Z. (1999) *Oncogene* 18, 6104–6111,
42 Casola, A., Garofalo, R. P., Haeberle, H., Elliott, T., Jamaluddin, M., Brasier, A. R (2001), *J Virol* 75, 6428–6439.

What is claimed:

1. A method of treating lung inflammation in a subject comprising:
   administering butylated hydroxyanisol to the subject in an amount effective to treat lung inflammation.

2. The method according to claim 1, wherein the butylated hydroxyanisol inhibits RANTES gene expression.

3. The method according to claim 1, wherein the butylated hydroxyanisol inhibits RANTES protein secretion.

4. The method according to claim 1, wherein the butylated hydroxyanisol inhibits interferon regulatory factor activation.

5. The method according to claim 4, wherein the butylated hydroxyanisol inhibits IRF-1 gene expression.

6. The method according to claim 4, wherein the butylated hydroxyanisol inhibits IRF-7 gene expression.

7. The method according to claim 4, wherein the butylated hydroxyanisol inhibits IRF-3 nuclear translocation.

8. The method according to claim 5, wherein the butylated hydroxyanisol blocks a molecule binding to the gamma interferon activated sequence of IRF-1.

9. The method according to claim 8, wherein the molecule is STAT-1.

10. The method according to claim 8, wherein the molecule is STAT-3.

11. The method according to claim 6, wherein the butylated hydroxyanisol blocks a molecule binding to the interferon stimulated response element of IRF-7.

12. The method according to claim 11, wherein the molecule is STAT-2.

13. The method according to claim 11, wherein the molecule is STAT-1.

14. The method according to claim 11, wherein the molecule is IRF-1.

15. The method according to claim 11, wherein the molecule is IRF-9.

16. The method according to claim 1, wherein the administering comprises:
   contacting an alveolar cell of the subject with the butylated hydroxyanisol.

17. The method according to claim 16, wherein the subject is a human.

18. A method of inhibiting interferon regulatory factor activation in an alveolar cell comprising:
   contacting the alveolar cell with butylated hydroxyanisol in an amount effective to inhibit interferon regulatory factor activation.

19. The method according to claim 18, wherein the butylated hydroxyanisol inhibits RANTES gene expression.

20. The method according to claim 18, wherein the butylated hydroxyanisol inhibits RANTES protein secretion.

21. The method according to claim 18, wherein the butylated hydroxyanisol inhibits IRF-1 gene expression.

22. The method according to claim 18, wherein the butylated hydroxyanisol inhibits IRF-7 gene expression.

23. The method according to claim 18, wherein the butylated hydroxyanisol inhibits IRF-3 nuclear translocation.

24. The method according to claim 21, wherein the butylated hydroxyanisol blocks a molecule binding to the gamma interferon activated sequence of IRF-1.

25. The method according to claim 24, wherein the molecule is STAT-1.

26. The method according to claim 24, wherein the molecule is STAT-3.

27. The method according to claim 22, wherein the butylated hydroxyanisol blocks a molecule binding to the interferon stimulated response element of IRF-7.

28. The method according to claim 27, wherein the molecule is STAT-2.

29. The method according to claim 27, wherein the molecule is STAT-1.

30. The method according to claim 27, wherein the molecule is IRF-1.

31. The method according to claim 27, wherein the molecule is IRF-9.

32. The method according to claim 18, wherein the subject is a human.

33. A method according to claim 18, wherein the alveolar cells are present in a human subject and wherein said contacting comprises administering a therapeutically effective amount of the butylated hydroxyanisol to the human subject.

* * * * *